(12) United States Patent
Mackel et al.

(10) Patent No.: US 9,896,480 B2
(45) Date of Patent: *Feb. 20, 2018

(54) INTEGRIN RECEPTOR ANTAGONISTS AND THEIR METHODS OF USE

(75) Inventors: Michael John Mackel, Portland, OR (US); John Y. Park, Santa Ana, CA (US); Hampar L. Karageozian, San Juan Capistrano, CA (US); Vicken H. Karageozian, San Juan Capistrano, CA (US)

(73) Assignee: Allegro Pharmaceuticals, Inc., San Juan Capistrano, CA (US)

( * ) Notice: Subject to any disclaimer, the term of this patent is extended or adjusted under 35 U.S.C. 154(b) by 434 days.

This patent is subject to a terminal disclaimer.

(21) Appl. No.: 13/467,995

(22) Filed: May 9, 2012

(65) Prior Publication Data

US 2013/0129621 A1 May 23, 2013

Related U.S. Application Data

(63) Continuation-in-part of application No. 12/943,900, filed on Nov. 10, 2010, now Pat. No. 9,018,352, and a continuation-in-part of application No. PCT/US2010/056277, filed on Nov. 10, 2010.

(60) Provisional application No. 61/484,194, filed on May 9, 2011, provisional application No. 61/486,195, filed on May 13, 2011, provisional application No. 61/259,748, filed on Nov. 10, 2009, provisional application No. 61/643,118, filed on May 4, 2012.

(51) Int. Cl.
| | | |
|---|---|---|
| A61K 38/06 | (2006.01) |
| C07K 5/09 | (2006.01) |
| A61K 51/08 | (2006.01) |
| C07K 7/06 | (2006.01) |
| C07K 7/64 | (2006.01) |
| A61K 9/08 | (2006.01) |
| A61K 38/08 | (2006.01) |
| A61K 38/12 | (2006.01) |
| A61K 38/17 | (2006.01) |
| A61K 39/395 | (2006.01) |
| A61K 51/06 | (2006.01) |
| A61L 26/00 | (2006.01) |
| A61L 27/00 | (2006.01) |
| A61L 27/22 | (2006.01) |
| A61L 31/04 | (2006.01) |
| G01N 1/00 | (2006.01) |
| A61K 47/64 | (2017.01) |
| A61K 9/06 | (2006.01) |

(52) U.S. Cl.
CPC .............. *C07K 5/0817* (2013.01); *A61K 9/08* (2013.01); *A61K 38/06* (2013.01); *A61K 38/08* (2013.01); *A61K 38/12* (2013.01); *A61K 38/1709* (2013.01); *A61K 39/3955* (2013.01); *A61K 47/64* (2017.08); *A61K 51/065* (2013.01); *A61K 51/082* (2013.01); *A61K 51/088* (2013.01); *A61L 26/00* (2013.01); *A61L 27/00* (2013.01); *A61L 27/227* (2013.01); *A61L 31/043* (2013.01); *C07K 7/06* (2013.01); *C07K 7/64* (2013.01); *G01N 1/00* (2013.01); *A61K 9/06* (2013.01); *A61L 2300/252* (2013.01)

(58) Field of Classification Search
None
See application file for complete search history.

(56) References Cited

U.S. PATENT DOCUMENTS

| | | | |
|---|---|---|---|
| 5,635,477 A | * | 6/1997 | Degrado .................. C07K 7/56 514/14.9 |
| 6,087,330 A | | 7/2000 | Kogan et al. |
| 6,331,285 B1 | | 12/2001 | Sharma |
| 6,500,924 B1 | | 12/2002 | Brooks et al. |
| 6,863,886 B2 | | 3/2005 | Karageozian et al. |

(Continued)

FOREIGN PATENT DOCUMENTS

| | | |
|---|---|---|
| JP | 08-119991 | 5/1996 |
| JP | 2002534132 A | 10/2002 |

(Continued)

OTHER PUBLICATIONS

Larson, Richard S. (Journal of Virology 79(12), 7319-7326, 2005.*
Men, 2005, Rapid Commun. Mass Spectrum. 19: 23-30 (Year: 2005).*
Barker, Peter L. et al.,"Antiplatelet and Antithrombotic Agents: From Viper Venom Proteins, to Peptides and Peptidomimetics, to Small Organic Molecules," Advances in Medicinal Chemistry, vol. 3, pp. 57-111. 1995.

(Continued)

*Primary Examiner* — Satyanarayana R Gudibande
(74) *Attorney, Agent, or Firm* — Robert D. Buyan; Stout, Uxa & Buyan, LLP

(57) ABSTRACT

Compounds comprising R-G-Cysteic Acid (i.e., R-G-NH—CH(CH$_2$—SO$_3$H)COOH or Arg-Gly-NH—CH(CH$_2$—SO$_3$H)COOH) and derivatives thereof, including pharmaceutically acceptable salts, hydrates, stereoisomers, multimers, cyclic forms, linear forms, drug-conjugates, prodrugs and their derivatives. Also disclosed are methods for making and using such compounds including methods for inhibiting integrins including but not necessarily limited to $\alpha_5\beta_1$-Integrin, $\alpha_v\beta_3$-Integrin and $\alpha_v\beta_5$-Integrin, inhibiting cellular adhesion to RGD binding sites, preventing or treating viral or other microbial infections, inhibiting angiogenesis in tumors, retinal tissue or other tissues or delivering other diagnostic or therapeutic agents to RGD binding sites in human or animal subjects.

28 Claims, 21 Drawing Sheets

(56) References Cited

U.S. PATENT DOCUMENTS

| | | |
|---|---|---|
| 7,070,936 B1 | 7/2006 | Hangauer et al. |
| 2002/0115823 A1 | 8/2002 | Wakimasu et al. |
| 2003/0059422 A1 | 3/2003 | Sharma |
| 2003/0139342 A1 | 7/2003 | McCuen |
| 2003/0166004 A1 | 9/2003 | Gyuris |
| 2003/0170250 A1 | 9/2003 | Ezrin et al. |
| 2004/0072315 A1* | 4/2004 | Lu et al. ............... 435/184 |
| 2006/0104898 A1 | 5/2006 | Hallahan et al. |
| 2006/0106196 A1 | 5/2006 | Gaudernack et al. |
| 2009/0088377 A1 | 4/2009 | Quraishi et al. |

FOREIGN PATENT DOCUMENTS

| | | |
|---|---|---|
| JP | 2002326949 | 11/2002 |
| WO | WO9422910 A1 | 10/1994 |
| WO | WO9963084 A1 | 12/1999 |
| WO | WO2006017619 A2 | 2/2006 |
| WO | WO2008134761 A2 | 11/2008 |
| WO | WO2011060104 A2 | 5/2011 |

OTHER PUBLICATIONS

Harris et al. 'Radiolabeled Divalent Peptidomimetic Vitronectin Receptor Antagonists as Potential Tumor Radiotherapeutic and Imaging Agents' Bioconjugate Chem (2007) vol. 18 p. 1266-1279; abstract, p. 1266, col. 2, para 1, Figs. 1-2, 11.

Li et al. '64Cu-Labeled Tetrameric and Octameric RGD Peptides for Small-Animal PET of Tumor alphavbeta3 1ntegrin Expression' J Nuclear Medicine (2007) vol. 48 p. 1162-1171; abstract, Fig. 1.

Chen et al. 'Synthesis and Biological Evaluation of Dimeric RGD Peptide-Paclitaxel Conjugate as a Model for Integrin-Targeted Drug Delivery' J Med Chem (2005) vol. 48 p. 1098-1106; abstract, Fig. 1.

Schornberg et at 'a5b1-Integrin controls ebolavirus entry by regulating endosomal cathepsins' PNAS (2009) vol. 106 p. 8003-8008; abstract.

Eichhorn et al. 'Angiogenesis in cancer: molecular mechanisms, clinical impact' Langenbecks Arch Surg (2007) vol. 392 p. 371-379; p. 374, col. 2, para 2, p. 375, col. 2, para 2.

Miyamoto et al. 'Integrins Can Collaborate with Growth Factors for Phosphorylation of Receptor Tyrosine Kinases and MAP Kinase Activation: Roles of Integrin Aggregation and Occupancy of Receptors' J Cell Bioi (1996) vol. 135 p. 1633-1642; abstract.

International Search Report and Written Opinion, PCT/US2012/037177, dated Aug. 14, 2012.

Humphries, M.J., J. Cell Sci., (1990) 97: 585-592.

Olivera, L.B., et al., RGD Peptide-Assisted Vitrectomy to Facilitate Induction of a Posterior Vitreous Detachment: a New Principle in Pharmacological Vitreolysis Current Eye Research (8):333-40 (Dec. 25, 2002).

Foos, R Y., Invest. Opthalmol. Vis. Sci. (1972) vol. 11 No. 10, 801-808.

Hershkoviz, S. M., et al., Invest. Ophthalmol. Vis. Sci., (1994), 35, 2585-2591.

Jiang D., Annu. Rev. Cell. Dev. Biol. (2007) 23: 435-461.

Hiroshi Mochimaru et al., Invest. Ophthalmol. Vis. Sci. (2009) 50: 4410-4415.

Michael A. Dechantsreiter, et al., J. Med. Chem. (1999) 42:3033-3040.

Hynes, R.A., et al., Cell (1992) 68: 303-322.

M. A. Buerkle et al., British J. Cancer (2002) 86: 788-795.

Eileen M. Finnegan et al., Am. J. Physiol. Heart Circ. Physiol., (2007) 293: H1038-H1045.

Pina M. Cardarelli et al., J. Biol. Chem. (1994) 269:18668-18673.

H.D. Maynard, J.A. Hubbell, Acta Biomaterialia (2005) 1: 451-459.

Greene's Protective Groups in Organic Synthesis by Peter G.M. Wuts and Theodora W. Greene, (2nd edition) J. Wiley & Sons, 1991.

Ruoslahti, E., J. Clin. Invest. (1991) vol. 87: 1-5.

Sebag J., Eye (1992), 6: 541-552.

Elner, S.G.,et al., IOVS (1996) 37:696-701.

Kelly N.E., et al., Arch. Ophthalmol. (1991) 109, 654-659.

Curtis,T.M.et al., Am. J. Physiol. , (1995) 269: L248-L260.

Tezel, T.H. et al, Retina (1998) 18: 7-15; and Verstraeten,T.C,et al., .Arch. Ophthalmol. (1993)111: 849-854.

Han D.P., et al., Arch. Ophthalmol. (1998) 106: 998-1000.

Trese M.T., Eye. (2002) 16: 365-368.

Gandorfer A., et al., Am. J. Ophthalmol. (2002) 133: 156-159.

Hesse L., et al., Eye Res. (2000) 70: 31-39.

Cindy K. Bahler et al., Invest. Ophthalmol. Vis. Sci. (2004) 45: 2246-2254.

Nickerson, C., et al., in J. Biomechanics, (2008) 41: 1840-1846.

Cheryl R. Hann, et al.,Ophthalmic Res. (2001) 33: 314-324.

Oshitari, T, et al., Am. J. Ophthalmol. (2007) 143:363-365.

Mark S. Filla, et al., Invest. Ophthalmol. Vis. Sci. (2002) 43:151-161.

Gehlsen K.R., et al., J. Cell. Biol. (1988) 106: 925-930.

Pierschbacher, M.D., et al., J. Biol. CHem., (1987) 262: 17294-17298.

Zhou L.L., et al., IOVS. (1996) 37: 104-113.

Nip, J., J. Clin. Invest., (1992) 90: 1406-1413.

MP Lutolf, et al., Proc. Nat. Acad. Sci. (2003) 100: 5413-5418.

MP Lutolf, et al., Nature Biotechnol. (2003) 21: 513-518).

Rong, L. et al., Invest. Ophthalmol. Vis. Sci. (2009) 50: 5988-5996.

Peter C. Brooks, et al., J. Clin. Invest., (1995) 96: 1815-1822.

Lehmann, M., Cancer Res., (1994), 54: 2102-2107.

Asymmetric Synthesis by Von G. M. Coppola and H. F. Schuster; John Wiley & Sons, New York 1987.

M. Rafiuddin Ahmed et al., Brain Res. (2003) 993:208-216.

Knudson, W. et al, Matrix Bio. (2002), 21: 15-23).

Karmali, P. et al., Targeting of albumin-embedded paclitaxel nanoparticles to tumors; Nanomedicine, vol. 5, No. 1 (Mar. 1, 2009).

Arrowsmith, J. et al., Antitumor Imidazotetrazines. 41. Conjugation of the Antitumor Agents Mitozolomide and Temozolomide to Peptides and Leitropsins Bearing DNA Major and Minor Groove-Binding Structural Motifs; J. Med. Chem., vol. 45, pp. 541-5462 (Dec. 5, 2002).

Lijie Men et al., Further studies on the fragmentation of protonated ions of peptides containing aspartic acid, glutamic acid, cysteine sulfinic acid, and cysteine sulfonic acid; Rapid Communications in Mass Spectromotry, vol. 19, No. 1, p. 25 (Jan. 15, 2005).

Atassi, M.Z. et al., "Enzymic and Immunochemical Properties of Lysozyme, XIII. Accurate Delineation of the Reactive Site Around the Disulfide 6-127 by Immunochemical Study of β-Propiolactone Lysozyme Derivative and of Synthetic Disulfide Peptides", Biochimica et Biophysica Acta, 420 (1976), pp. 358-375.

Office Action dated Nov. 11, 2014 in related Japanese Patent Application No. 2012-538958.

Office Action dated Sep. 12, 2014 in related Russian Patent Application No. 2012118503.

"Allegro Ophthalmics Announces Presentation of Key Data on New Class of Vascular Eye Disease Therapy", Press Release.

Hugo E. Sepulveda-Vazquez, et al., "Intravitreal Injection of Integrin Peptide ALG-1001 for the Induction of Posterior Vitreous Detachment in Rabbit Eyes", Investigative Ophthalmology & Visual Science, vol. ARVO, 2012.

European Search Report and Search Opinion dated Feb. 13, 2015 in related European Application 12782195.7.

Lisa D. Volk, et al., "Synergy of Nab-Paclitaxel and Bevacizumab in Eradicating Large Orthotopic Breast Tumors and Preexisting Metastases," Neoplasia, vol. 13, No. 4, Apr. 2011, pp. 327-338.

Gesine B. Jaissle M.D. et al., "Suppression of Melanoma-Associated Neoangiogenesis by Bevacizumab," Arch Dermatol, vol. 144, No. 4, Apr. 2008, pp. 525-527.

Jian-Ping Xiong et al., "Crytal Structure of the Extracellular Segment of Integrin αVβ3 in Complex with an Arg-Gly-Asp Ligand," Science, vol. 296, Apr. 2002, pp. 151-155.

Office Action dated Feb. 23, 2016 in corresponding Japanese Patent Application No. 2014-510451.

\* cited by examiner

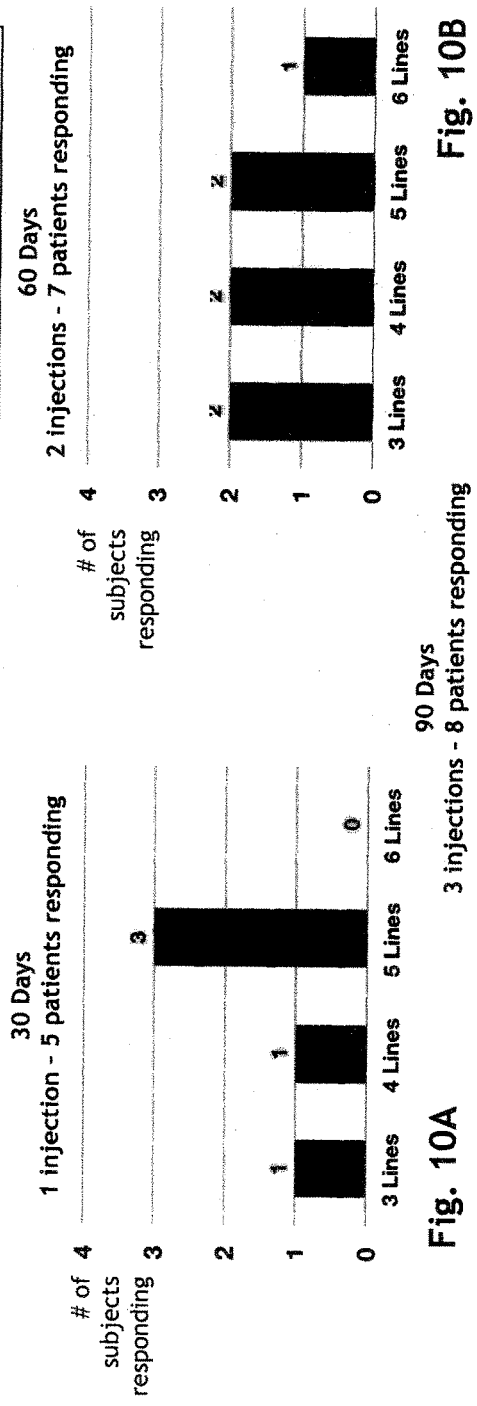
Fig. 10A, Fig. 10B, Fig. 10C  Patient benefit as measured by improvement in BCVA seen at Day 30 with increased benefit at Day 60 and Day 90

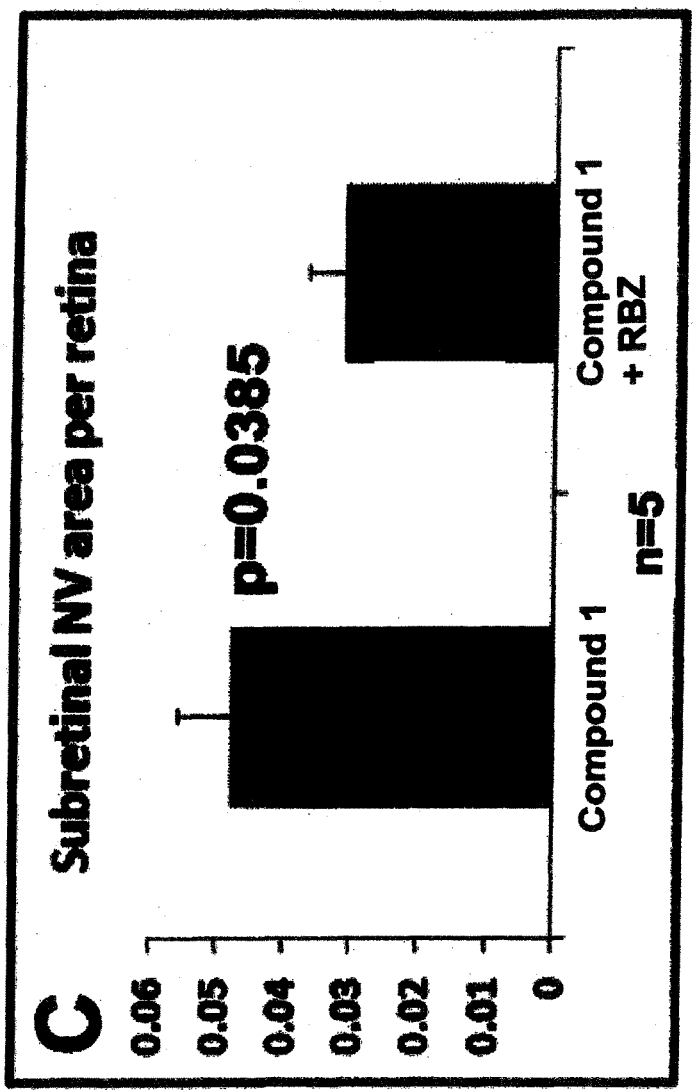

INTEGRIN RECEPTOR ANTAGONISTS AND THEIR METHODS OF USE

RELATED APPLICATIONS

This application claims priority to each of U.S. Provisional Patent Application Ser. No. 61/484,194 filed May 9, 2011, 61/486,195 filed May 13, 2011 and 61/643,118 filed May 4, 2012, the entire disclosure of each such provisional patent application being expressly incorporated herein by reference. Additionally, this application is a continuation in part of a) copending PCT International Patent Application No. PCT/US2010/056277 filed Nov. 10, 2010 and b) U.S. patent application Ser. No. 12/943,900 filed Nov. 10, 2010, both of which claim priority to U.S. Provisional Patent Application Ser. No. 61/259,748 filed Nov. 10, 2009. The entire disclosure of each of the foregoing patent applications is expressly incorporated herein by reference.

FIELD OF THE INVENTION

The present invention relates generally to the fields of chemistry and medicine and more particularly to integrin receptor antagonists and their methods of use.

BACKGROUND OF THE INVENTION

The RGD tripeptide sequence is found in a number of proteins, where it plays a role in cell adhesion. Examples of proteins in which the RGD tripeptide sequence is present include collagens, fibronectin, vitronectin, von Willebrand factor (VWF), certain disintegrins, and certain discoidins.

Integrins are heterodimeric cell surface receptors which mediate adhesion between cells and the extracellular matrix (ECM) by binding to ligands having an exposed RGD sequence. Normal integrin-RGD binding is believed to play a role in gene expression involved in cell growth, migration, and survival. Faulty regulation of such cell growth, migration, and survival can result in a number of disease states including thrombosis, inflammation, and cancer. Thus, RGD peptides have been investigated as potential mimics of cell adhesion proteins and for their ability to bind to integrins for therapeutic purposes such as inhibiting cell adhesion, cell migration, cell proliferation, cell differentiation, apoptosis, angiogenesis, tumorigenesis, for inhibiting entry of microbes into cells, for the use in their multimeric form as internal radiotherapeutic agents as well as cancer imaging agents and for their anti-cancer drug carrying abilities.

In the eye, integrins affect a number of processes including ocular development, cell migration, healing and some pathologic processes. Integrins may also modulate inflammation and thrombosis in ocular tissue. Intravitreally injected RGD peptide has also been reported to cause posterior vitreoretinal detachment in an animal model and, thus, may be useful in the treatment of certain retinal disorders and/or to facilitate removal of the vitreous body in a vitrectomy procedure. See Olivera, L. B., et al., *RGD Peptide-Assisted Vitrectomy to Facilitate Induction of a Posterior Vitreous Detachment: a New Principle in Pharmacological Vitreolysis*; Current Eye Research (8):333-40 (Dec. 25, 2002).

Integrins are also known to be used by various enveloped and non-enveloped viruses and bacteria in infecting host cells. Schornberg, Kathryn L.; $\alpha_5\beta_1$-*Integrin Controls Ebolavirus Entry by Regulating Endosomal Cathespins*; Proc. Nat. Acad. Sci. USA; Vol. 106, No. 19, pp. 8003-8008 (2009)

SUMMARY OF THE INVENTION

The present invention provides novel compounds comprising R-G-Cysteic Acid (i.e., R-G-NH—CH(CH$_2$—SO$_3$H)COOH or Arg-Gly-NH—CH(CH$_2$—SO$_3$H)COOH) and derivatives thereof (including pharmaceutically acceptable salts, hydrates, stereoisomers, multimers, cyclic forms, linear forms, drug-conjugates, pro-drugs and their derivatives).

The present invention also provides compositions and methods for therapeutic or prophylactic inhibition of integrin receptors in human or animal subjects. Such integrin receptor inhibition may be used for treatment or prevention of neovascularization or blood vessel formation in tumors or other tissues (e.g., the retina of the eye), to treat or prevent viral diseases, deter viral various disorders including diabetic retinopathy and other conditions involving unwanted neovascularization to prevent or treat inhibiting cellular adhesion to RGD binding sites or delivering other diagnostic or therapeutic agents to RGD binding sites in human or animal subjects by administering to the subject an effective amount of a composition comprising an R-G-Cysteic Acid peptide or a derivative thereof (including pharmaceutically acceptable salts, hydrates, stereoisomers, multimers, cyclic forms, linear forms, drug-conjugates, pro-drugs and their derivatives). Specific examples of R-G-Cysteic Acid peptide of this invention include a linear form of Arg-Gly-NH—CH(CH$_2$—SO$_3$H)COOH (example referred to herein as Compound 1) and a cyclic form of Arg-Gly-NH—CH(CH$_2$—SO$_3$H)COOH) (example referred to herein as Compound 2).

General formulas for R-G-Cysteic Acid derivatives of the present invention include but are not limited to compounds having General Formulas I-VII as follows:

General Formula I:

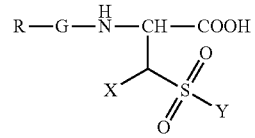

where X is selected from: H, C$_1$-C$_6$ alkyl, Ph or SO$_3$H and Y=OH or NH$_2$.

General Formula II:

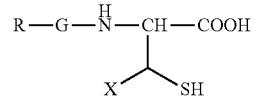

where X is selected from: H, C$_1$-C$_6$ alkyl, Ph or SO$_3$H.

General Formula III:

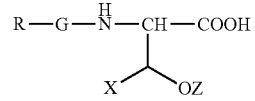

where X is selected from: H, C$_1$-C$_6$ alkyl, Ph or SO$_3$H and wherein Z is selected from: H or SO$_3$H General Formula IV:

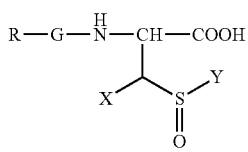

where X is selected from: H, $C_1$-$C_6$ alkyl, Ph or $SO_3H$; Y is selected from OH or $NH_2$.

General Formula V:

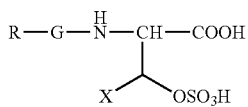

where X is selected from: H, $C_1$-$C_6$ alkyl, Ph or $SO_3H$.

General Formula VI:

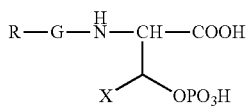

where X is selected from: H, $C_1$-$C_6$ alkyl, Ph or $SO_3H$.

$X_1$—R-G-Cysteic Acid-X    General Formula VII:

where X and are selected from: cyclic or linear -Phe-Val-Ala, -Phe-Leu-Ala, -Phe-Val-Gly, -Phe-Leu-Gly, -Phe-Pro-Gly, -Phe-Pro-Ala, -Phe-Val, or any salt of any combination of the D-isomer or L-isomer of: Arg, Gly, Cysteic, Phe, Val, Ala, Leu, Pro, Thr.

Examples of cyclic forms of General Formula VII include but are not necessarily limited to:

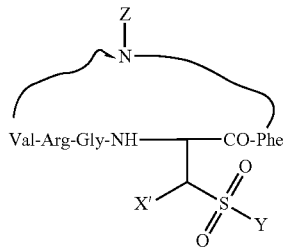

where X' is selected from: H, $C_1$-$C_6$ alkyl, Ph or $SO_3H$ and Z is selected from H or Me; Y is selected from OH, $NH_2$.

Sulfonic acids are stronger acids than corresponding carboxylic acids. This higher polarity of the sulfonic acid group leads to stronger intermolecular bonding. For example, R-G-Cysteic acid, which has a more polarized O—H bond, may form stronger hydrogen bonds than R-G-Aspartic acid (RGD peptide), which has a relatively less polarized O—H bond, with the amide groups of the proteins in the integrin binding site and/or have stronger interactions with metal ions complexed in the integrin binding site.

As described in more detail elsewhere herein, one specific example of General Formula VII, Glycinyl-Arginyl-Glycinyl-Cysteic-Threonyl-Proline-COOH (GRG Cysteic Acid TP; referred to below as Compound 1) was synthesized and tested in animals and found to be effective in inducing posterior vitreous detachment (PVD) from retina surface by inhibiting integrin-extracellular matrix (ECM) interactions. As described also in more detail elsewhere herein, Compound 1 was tested in a model of wound healing using human umbilical vein endothelial cells (HUVEC) and was shown to inhibit cell adhesion by 74% in 12 hours compared to an inhibition of 40% by a cyclic-RGD peptide. These studies suggest and corroborate the rationale that Glycinyl-Arginyl-Glycinyl-Cysteic-Threonyl-Proline-COOH may bind to integrin even more strongly than RGD peptides themselves.

The RG Cysteic Acid peptide sequence, which can be in either L-form or D-form, is a competitive inhibitor of integrin-ECM interactions. The RG Cysteic Acid peptide sequence can be of protease-resistant derivatives or of cyclic derivatives or of pro-drug derivatives or associated with drug delivery systems or of monoclonal antibodies.

The compositions of the present invention are useable to inhibit angiogenesis, which can be useful for treating inflammation, wound-healing, thrombosis, cancer metastases and tumors. Further useful application can be found in ophthalmology including the treatment of, proliferative or non-proliferative diabetic retinopathy, liquefaction of the vitreous, induction of posterior vitreo-retinal detachment (PVD), pathogenesis of vitreoretinal diseases, such as idiopathic macular hole, macular edema, floaters, vitreomacular traction, age related macular degeneration, wet macular degeneration, choroidal neovascularization, vitreoretinal surgery, vein occlusion, and prevention of scar formation in glaucoma surgery. Still further, multimeric and/or radiolabeled compositions of the present invention are useable as diagnostic/imaging agents for the detection of tumors and radiotherapeutic agents for the treatment of tumors and as anti-cancer drug carriers due to their tumor directing properties.

Biomaterials incorporating an RG CYSTEIC ACID peptide can also provide a synthetic adhesive microenvironment for the long term survival and growth of cells and for the engineering of living tissues for applications in tissue engineering and regenerative medicine. Through their property of binding integrin adhesion receptors, RG CYSTEIC ACID peptides can provide an adhesion-promoting signal when it is tethered onto a biomaterial or scaffold. RG CYSTEIC ACID-based materials mediate cell adhesion, spreading, and migration of cells. In addition, integrin-mediated cell adhesion promotes cell proliferation and survival and plays a key role in assembly and organization of multicellular structures and tissues.

Drugs for the treatment of macular degeneration like Lucentis and Avastin are based on inhibiting VEGF, which otherwise causes the growth of new vessels, angiogenesis, and consequently contributes macular edema. It has been known that a small peptide RGD can induce apoptosis by inhibiting cell attachment to extracellular matrix[1] by competitive binding as shown in U.S. Pat. No. 6,500,924 to Brooks et al.

The RGD peptide binding or recognition motif can be found in the proteins of extracellular matrix and integrins which link the intracellular cytoskeleton of cells with the ECM by recognizing the RGD adhesion epitopes. See, for example, Foos, R Y., Invest. Opthalmol. Vis. Sci. (1972) 11, 801-808. Cells, without the attachment to the ECM, normally undergo apoptosis.

In general, interactions between fibroblasts and glycoprotein components of extracellular matrix cause a major scar formation mediated primarily by the RGD containing amino acid sequence interacting on the cell surface integrins. It has also been known that the RGD sequence is involved in cell-ECM interactions during inflammatory and homeostatic reactions (see Hershkoviz, S. M., et al., Invest. Ophthalmol. Vis. Sci., (1994), 35, 2585-2591) and the integrins play an important role in cell migration in wound healing or pathologic processes and modulating inflammation and thrombosis. Thus, potent integrin antagonists, like RGD peptides, might be very useful as pharmacologic agent as anti-inflammatory, anti-metastatic or anti-thrombotic agents (see Elner, S. G. and Elner, V. M., IOVS (1996) 37:696-701. It is also reported in literature that CD44 receptor for hyaluronic acid mediates cell-cell and cell-matrix interactions through its affinity for hyaluronic acid, and possibly also through its affinity for other ligands such as osteopontin, collagens, and matrix metalloproteases (MMPs).

Adhesion with hyaluronan plays an important role in cell migration, tumor growth and progression and also involved in lymphocyte activation, recirculation and homing, and hematopoiesis. Altered expression or dysfunction causes numerous pathogenic phenotypes (see for example, Jiang D., Annu. Rev. Cell. Dev. Biol. (2007) 23: 435-461; and Knudson, W. et al, Matrix Bio. (2002), 21: 15-23).

Recently, it has been shown that the interaction of CD44 and cell-matrix components (e.g., HA) plays a significant role in the development of various inflammatory diseases and interruption of hyaluronan-CD44 interactions would lead to amelioration of choroidal neovascularization (see Hiroshi Mochimaru et al., Invest. Ophthalmol. Vis. Sci. (2009) 50: 4410-4415).

These evidences demonstrate that an adhesion molecule like RGD peptide or CD44 in cell-cell and cell-ECM interactions plays an important role in the development of numerous pathogenic diseases and the inhibition of the interactions can be a novel therapeutic target in treating and curing the diseases.

Synthetic peptides have also been shown to bind to integrins and growth factors. Cyclized pentapeptides containing RGD sequences have been found to inhibit binding of vitronectin to $\alpha_v\beta_3$ integin (see Michael A. Dechantsreiter, et al., J. Med. Chem. (1999) 42:3033-3040) and both vitronectin and fibronectin to $\alpha_v\beta_3$ and $\alpha_{IIb}\beta_3$ integrins (see Roland Haubner et al., J. Am. Chem. Soc., (1996)118:7461-7472). This inhibition has been shown to be useful in the treatment of multiple, unrelated diseases. In hamster studies, the cyclic pentapeptides delayed growth and metathesis of tumors in comparison with control animals (see M. A. Buerkle et al., British J. Cancer (2002) 86: 788-795). The pentapeptides have also been shown to reduce binding of sickle red blood cells to vascular endothelium and improved hemodynamic behavior (see Eileen M. Finnegan et al., Am. J. Physiol. Heart Circ. Physiol., (2007) 293: H1038-H1045). Another cyclic peptide containing the RGD sequence has shown strong binding to $\alpha4\beta1$, an integrin known to play a role in leucocyte binding in inflammatory and immune responses (see Pina M. Cardarelli et al., J. Biol. Chem. (1994) 269:18668-18673). A synthetic, sulfated tetrapeptide has been shown to strongly bind to VEGF (see Maynard, J. A. Hubbell, Acta Biomaterialia (2005) 1: 451-459).

In addition, in an important and useful application, a dimeric RGD peptide-drug conjugate has been shown to be useful for integrin-targeted drug delivery for tumor targeting (see Chen et al., J. Med. Chem., (2005) 48(4): 1098-1106).

In another equally important and useful application, multimeric radiolabeled RGD peptides have been shown to be useful as diagnostic/imaging agents for tumor detection and, as radiotherapeutic agents for tumor specific targeting and treatment by targeting the integrin $\alpha_v\beta_3$ (see Zi-Bo Li et al., J. Nucl. Medicine, (2007) 48: 1162-1171).

In ophthalmology, scar formation in wound healing by fibroblast is one of the major problems, particularly in glaucoma. This arises from interactions between fibroblast and glycoprotein components of ECM. Recognition of ECM glycoproteins occurs via cell surface integrins that are specific for adhesion epitopes, such as the Arg-Gly-Asp (or RGD) sequence. The RGD sequence, which is present in several matrices of plasma proteins, including fibronectin (FN) and vitronectin (VN), is involved in cell-ECM interactions that occur during inflammatory and homeostatic reactions. Inhibition of the interactions between fibroblast and glycoproteins of ECM alleviated the scar formation (see Rami Hershkoviz et al., Invest. Ophthalmol. Vis. Sci. (1994) 35: 2585-2591).

The collagen fibrils of the posterior vitreous cortex adhere to the vitreoretinal interface, specifically to the inner limiting lamina of the retina surface (see Sebag J., Eye (1992), 6: 541-552). The adherence at the vitreous base, the optic disc, along the major retinal vessels and in a facial manner to the entire posterior pole plays an important role in the pathogenesis of vitreoretinal diseases, such as idiopathic macular hole, vitreomacular traction, proliferative diabetic retinopathy, etc. (Akiba J. Quiroz M. A., et al., Ophthalmol. (1990) 97, 1619-1655).

Angiogenesis inhibition is showing early promise with diabetic retinopathy and macular degeneration, which both result from an overgrowth of ocular blood vessels. In these disorders, the vessels interfere with normal structures in the eye, or they block light from reaching the back of the eye. The new blood vessels are themselves the primary pathology, and stopping blood vessel growth could prevent blindness. Thus, angioinhibition could result in not just a treatment of these disorders; it could be a cure. Furthermore, it has been postulated that separation of the vitreous from the retina can alleviate macular traction, reducing the risk of macular hole formation. Accordingly, the posterior vitreous detachment by the inhibition of fibronectin and laminin binding to the integrins on the vitreoretinal interface, may prevent retinal neovascularization in eyes with diabetic retinopathy and retinal vein occlusion (see Akiba J. Quiroz M A, Ophthalmol. (1990) 97, 1619-1655; Kelly N. E., et al., Arch. Ophthalmol. (1991) 109, 654-659; and Kado M, et al., Am. J. Ophthalmol. (1988) 105: 20-24).

In recent years, vitreous surgical procedures have been greatly improved to relieve vitreoretinal tractions and to reduce retinal edema. Despite continued improvement in surgical techniques and instrumentation, it still remains difficult to achieve an atraumatic removal of the vitreous cortex in some patients particularly in diabetic retinophatry and pediatric patients due to complications such as retinal breaks, retinal detachment and retinal nerve fiber damage (see Sebag J., Arch. Clin. Exp. Ophthalmol. (1987) 225: 89-93; and Han D. P., et al., Arch. Ophthalmol. (1998) 106: 998-1000) etc. Thus, a less traumatic approach to selectively cleave the vitreous interface without damaging the retina is highly desirable. In recent years, reports concerning a number of pharmacologic agents for the separation of the vitreoretinal interface have appeared in literature (see Trese M. T., Eye. (2002) 16: 365-368; Gandorfer A., et al., Am. J. Ophthalmol. (2002) 133: 156-159; and Hesse L., et al., Eye Res. (2000) 70: 31-39). The pharmacologic vitreolysis using enzymes such as hyaluronidase (see U.S. Pat. No. 6,863,886 to Karageozian et al.) and autologous plasmin (Sakuma T, et al., Nippon Ganka Gakkai Zassi (2003) 107: 709-718) have been explored to promote the digestion of extracellular matrix and to induce posterior vitreous detachment in the past. Yet, a non-specific destruction of adjacent tissues by the enzymes employed impedes success of their therapeutic application. In the last few years, a novel approach using non-enzymatic pharmacologic agents like urea (see Nickerson, C., et al., in J. Biomechanics, (2008) 41: 1840-1846, and in Macromol. Symp. (2005): 183-189) and RGD peptide (see Leonardo B. Oliviera, et al., Curr. Eye Res. (2002) 25: 333-340) has been investigated by concentrating on the separation of vitreoretinal interface. It has been shown that a synthetic analog of RGD peptide competes for the RGD motif of ECM proteins to disrupt integrin—ECM interactions and to loosen the attachments in-vitro (Williams J. A., Pathol. Bio. (1992) 40: 813-821; Gehlsen K. R., et al., J. Cell. Biol. (1988) 106: 925-930; Pierschbacher, M. D., et al., J. Biol. CHem., (1987) 262: 17294-17298; and Zhon L. L., et al., IOVS. (1996) 37: 104-113) and in-vivo. Thus, the intravitreal injection of soluble RGD peptides led to a release of RGD-epitopes from the insoluble ECM proteins of the retinal surface, consequently facilitating the non-enzymatic PVD in rabbit models. Clearly, these results indicate that the vitreoretinal interface involves integrin connection to RGD motif of ECM as well as adhesion of vitreous cortical collagens to the inner limiting lamella (ILL). RGD peptides and their derivatives promote migration of epithelial cells in a wound (see P. M. Mertz et al., J. Burn Care Res. (1996) 17: 199-206) and maintain their bioactivity when incorporated into synthetic biomaterials such as hydrogels (see M P Lutolf, et al., Proc. Nat. Acad. Sci. (2003) 100: 5413-5418; and M P Lutolf, et al., Nature Biotechnol. (2003) 21: 513-518), other polymer matrices (see Horng-Ban Lin et al., J. Biomed. Material. Res. (2004) 28: 329-342) or as surface films on hard substrates (D. M. Ferris et al., Biomaterials (1999) 20: 2323-2331). RGD peptides also promote increased adhesion of epithelial or endothelial cells to vascular prostheses (see K. Walluscheck et al., Eur. J. Vascular and Endovascular Surgery (1996) 12: 321-330) and other artificial organs (see Jeschke, Brigette, Biomaterials (2002) 23: 3455-3463) coated with the peptide sequence and have been shown to support nerve regrowth (see M. Rafiuddin Ahmed et al., Brain Res. (2003) 993:208-216). The prostheses's biologically active surface can contain synthetic resin fibers or polymers.

BRIEF DESCRIPTION OF THE FIGURES

FIGS. 10A through 10J are graphic and diagrammatic showing of the results of a human multiple dose clinical trial of Compound 1.

DETAILED DESCRIPTION AND EXAMPLES

Figure 1:
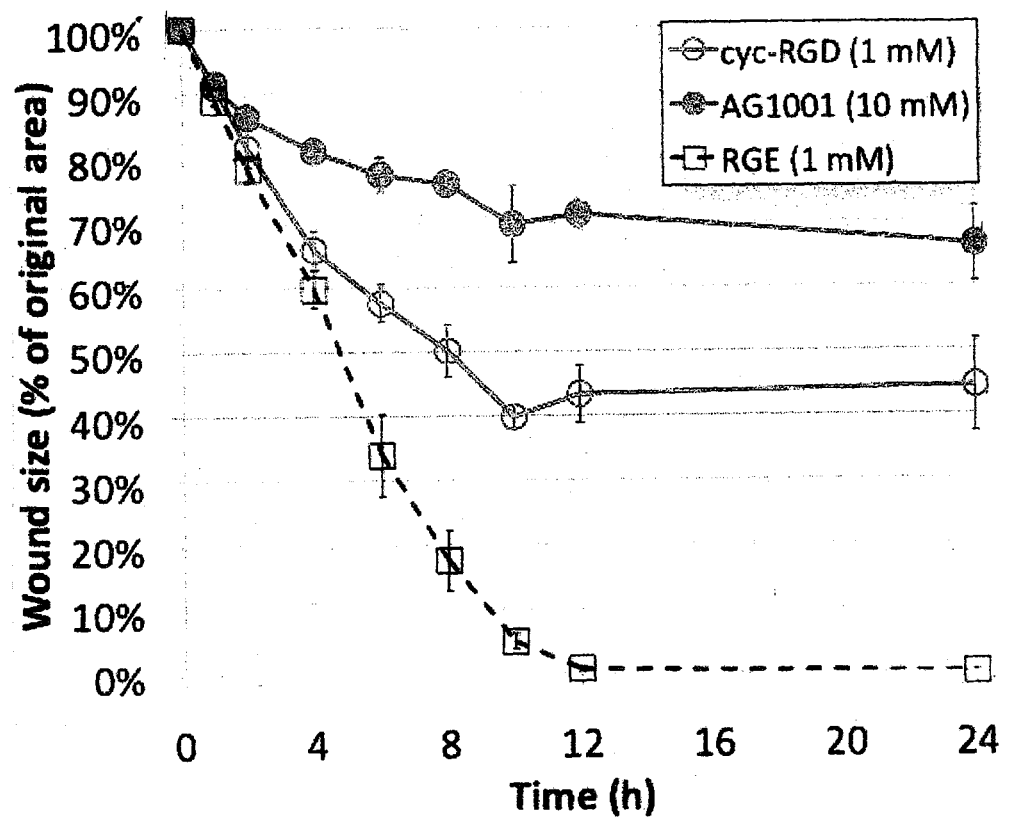
FIG. 1 shows the effect of three peptides, namely, cyclic-RGD-peptide, RG CYSTEIC ACID peptide (Compound 1) and RGE peptide, on the kinetics of wound healing.

The present invention provides novel compounds, including those of General Formulas I through VII above. Specific examples include linear form of Arg-Gly-NH—CH(CH$_2$—SO$_3$H)COOH (example referred to herein as Compound 1) and cyclic form of Arg-Gly-NH—CH(CH$_2$—SO$_3$H)COOH) (example referred to herein as Compound 2) as well as derivatives thereof, including pharmaceutically acceptable salts, hydrates, stereoisomers, multimers, cyclic forms, linear forms, multimeric forms, drug conjugates, pro-drugs and their derivatives.

Synthesis of Compounds 1 and 2

Conventional solid-phase peptide synthesis (SPPS; see R. B. Merrifield, *J. Am. Chem. Soc.* (1963) 85 (14): 2149-2154) known to a person of ordinary skill in the art maybe carried out. The SPPS is a preferred method of synthesis because of the high yields. In general, the first stage of the solid phase peptide synthesis technique consists of peptide chain assembly with protected amino acid derivatives on a polymeric support. The second stage of the technique is the cleavage of the peptide from the resin support with the concurrent cleavage of all side chain protecting groups to give the crude free peptide. The general principle of SPPS is one of repeated cycles of coupling-deprotection. The free N-terminal amine of a solid-phase attached peptide is coupled to a single N-protected amino acid unit. This unit is then deprotected, revealing a new N-terminal amine to which a further amino acid may be attached. See Asymmetric Synthesis by Von G. M. Coppola and H. F. Schuster; John Wiley & Sons, New York 1987 for synthesis, protection and deprotection strategies and Greene's Protective Groups in Organic Synthesis by Peter G. M. Wuts and Theodora W. Greene, (2nd edition) J. Wiley & Sons, 1991. for protection and deprotection strategies.

Of the two major used forms of solid phase peptide synthesis—Fmoc (9-fluorenylmethyloxycarbonyl; base labile alpha-amino protecting group) and t-Boc (t-butyloxycarbonyl; acid labile protecting group), Fmoc may be used preferably in the synthesis of the present peptides. Each method involves different resins and amino acid side-chain protection and consequent cleavage/deprotection steps. After cleavage from the resin, peptides are usually purified by reverse phase HPLC using columns such as C-18, C-8, and C-4.

An Example of Solid Phase Peptide Synthesis

The following is an outline of the synthetic steps for peptide synthesis on Wang resin as the solid support, using the base labile 9-fluorenylmethyloxycarbonyl (Fmoc) protecting group.

Fmoc Deprotection

Load 0.08 mmol of Fmoc-Pro-Wang resin into a fritted column equipped with a plastic cap. Wash the resin with 2×3-ml portions of DMF (dimethylformamide) for 1 minute each. Next, add about 3 ml of 20% piperidine in DMF and allow the Fmoc deprotection to continue for 15 minutes.

During this time, gently swirl or agitate the column to assure a complete mixing. After the reaction is complete (about 15 min.), drain the reaction column and wash the resin again with DMF (4×3 ml).

Amide Bond Coupling

The desired Fmoc-protected amino acid, Fmoc-Thr-tBu, (3 eq.; relative to resin loading indicated by supplier) and DIEA (6 eq.) in DCM (0.5 M with respect to the amino acid) are then added to the resin. The mixture is cooled at −20° C. for 20 minutes. Next, benzotriazol-1-yl-oxytripyrrolidino-phosphonium hexafluorophosphate (PyBOP), a peptide coupling reagent used in solid phase peptide synthesis (3 eq.) is added to the reaction. After shaking at −20° C. for 8 hours, the reaction mixture is drained and the resin is washed with DCM (3×).

After the Fmoc deprotection using 20% piperidine in DMF (15 min) and the wash with DMF (3×), the next Fmoc protected amino acid (3 eq.; relative to resin loading), PyBop (is coupled in the same manner as above.

Cleavage

In order obtain the peptide in the free acid form, the ester linkage is cleaved using strongly acidic conditions such as TFA (trifluoroacetic acid). Treat the resin with 2-3 ml of a solution of trifluoroacetic acid and water 95:5. Gently agitate the resin over a period of 25 minutes. Next, drain the column and carefully collect the filtrate into a glass collection vessel.

Synthesis of Compound 1 (GRG Cysteic Acid TP):

Compound 1

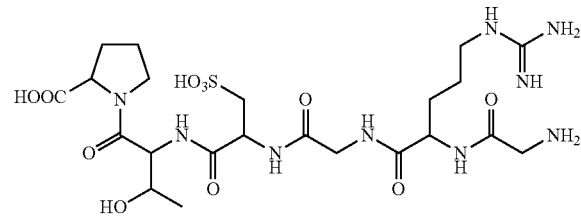

Step 1. Resin Loading: An o-chlorotrityl resin preloaded with proline is used as the starting material.
Step 2. Peptide assembly: Fmoc synthesis is used to assemble the peptide. Protected amino acids are activated with PyBOP and the terminal Fmoc groups removed with 20% piperidine in DMF. The following protected amino acids are used in the order in the order in which they appear:
  a. Fmoc-Thr-tBu (Fmoc threonine-t-butyl ester)
  b. Fmoc-cysteic acid-Pfp (Fmoc cysteic acid-pentafluorophenyl ester)
  c. Fmoc-Gly (Fmoc glycine)
  d. Fmoc-Arg-Pbf ($N_\alpha$-Fmoc-Nω-(2,2,4,6,7 pentamethyl-dihydrobenzofuran-5-sulfonyl)-L-arginine)
  e. Fmoc-Gly (Fmoc glycine)
Step 3. Peptide cleavage from Resin: The resulting peptide is cleaved from the solid support and the protecting groups removed with a solution of 85.5% TFA, 5% phenol, 2% water, 5% thioanisole, and 2.5% ethanedithiol.
Step 4. Purification: High Performance Liquid Chromatography (HPLC), is used to purify the resulting RG CYSTEIC ACID peptides.

Figure 2:
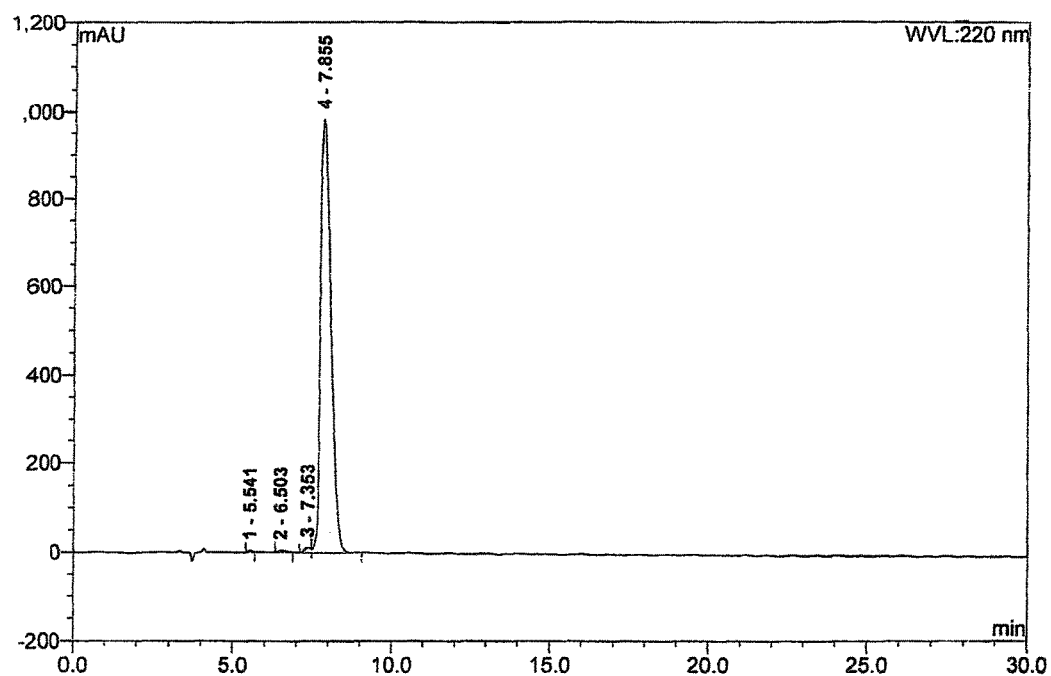
FIG. 2 shows and HPLC chromatogram of RG CYSTEIC ACID peptide (Compound 1).
Figure 3:
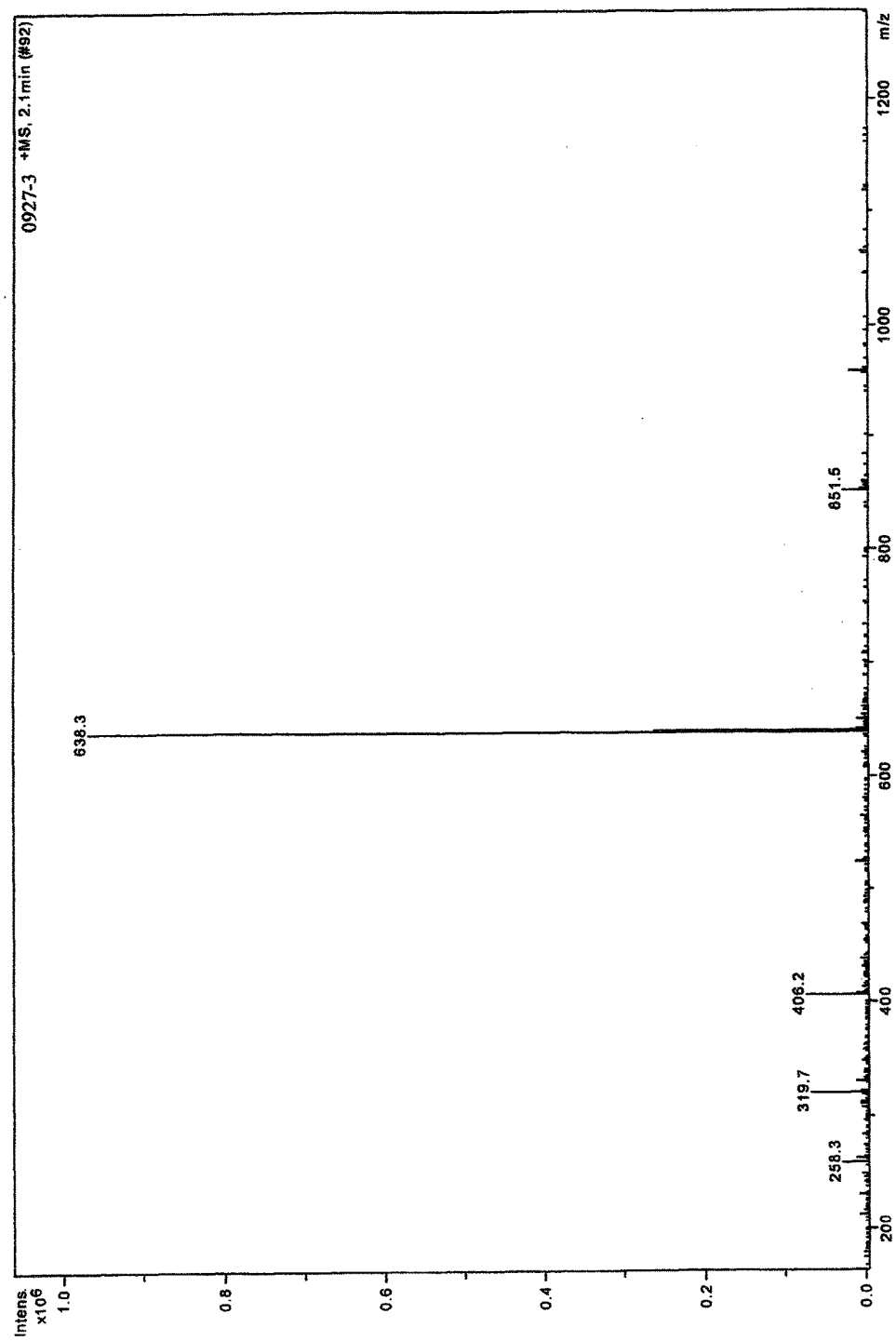
FIG. 3 shows an Electrospray mass chromatogram of RG CYSTEIC ACID peptide (Compound 1).

A quantity of Compound 1, prepared as described above, was analyzed by High Performance Liquid Chromatography to be >98% area/area in purity [HPLC conditions: Buffer A: 0.1% trifluoroacetic acid (TFA) in water, Buffer B: 0.1% TFA in acetonitrile, Mobile Phase (MP) A: 97% Buffer A and 3% Buffer B, Mobile Phase B: 79% Buffer A and 21% Buffer B, Mobile Phase C: 50% Buffer A and 50% Buffer B; for gradient see Table 1 below; flow rate: 1.0 mL/minute; column: Waters Symmetry® C18, 5μ, 4.6×250 mm; column temperature: 30° C.; detector: UV@220 nm; sample injection volume: 20.0 μL; sample preparation: 20 μL sample diluted with 1.0 mL Mobile Phase A (approximately 0.5 mg/mL)]. The corresponding HPLC chromatogram is shown in FIG. 2. In addition, based on the stepwise addition of the corresponding amino acids for the synthesis of the peptide sequence, the molecular weight of purified Compound 1 was determined by Electrospray Mass Spectrometry to be 638.3 amu (theoretical mass: 637.7 amu), confirming the identity of Compound 1. The Electrospray mass spectrogram of Compound 1 is shown in FIG. 3.

TABLE 1

Pump Gradient Program to detect Compound 1 by HPLC

| | | Pump Gradient Program | | |
|---|---|---|---|---|
| Step | Time | % MP A | % MP B | % MP C |
| 0 | 0.1 min | 100 | 0 | 0 |
| 1 | 60 min | 0 | 100 | 0 |
| 2 | 20 min | 0 | 0 | 100 |
| 3 | 15 min | 100 | 0 | 0 |

Synthesis of Compound 2 (Cyclo-RG CYSTEIC ACIDysteic Acid fN(CH₃)V):

Compound 2

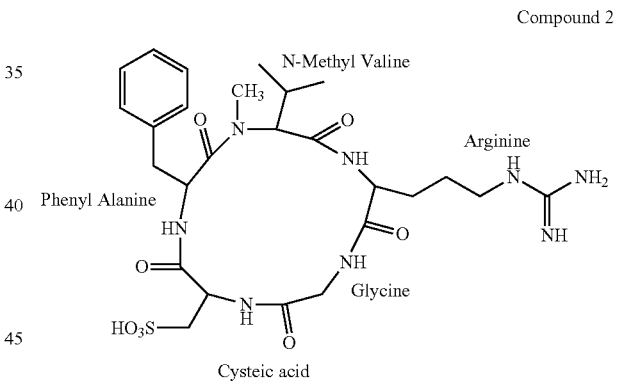

Step 1. Loading Resin: An o-chlorotrityl resin is used as the starting material. Fmoc-N□-methyl-L-Val is attached to the resin.
Step 2. Peptide Assembly: 2. Fmoc synthesis is used for the peptide assembly. Protected amino acids are activated with PyBOP and the terminal Fmoc groups removed with 20% piperidine in DMF. The following protected amino acids are used in the order in which they appear:
  a. Fmoc-Phe (Fmoc-phenyl alanine)
  b. Fmoc-cysteic acid-PfP (Fmoc-cysteic acid pentafluorophenyl ester)
  c. Fmoc-Gly (Fmoc-glycine)
  d. Fmoc-Arg-Pbf ($N_\alpha$-Fmoc-Nω-(2,2,4,6,7 pentamethyl-dihydrobenzofuran-5-sulfonyl)-L-arginine)
Step 3. Peptide cleavage from resin: The peptide is cleaved from the solid support using acetic acid/TFA/DCM (1:3:3)
Step 4. Cyclization and deprotection to desired cyclic peptide: Cyclization via in situ activation using diphenylphosphorylazide and sodium bicarbonate under high dilution.

The side chains are deprotected using 85.5% TFA, 5% phenol, 2% water, 5% thioanisole, 2.5% ethanedithiol.

Step 5. Purification: HPLC is used for purification.

Figure 4:
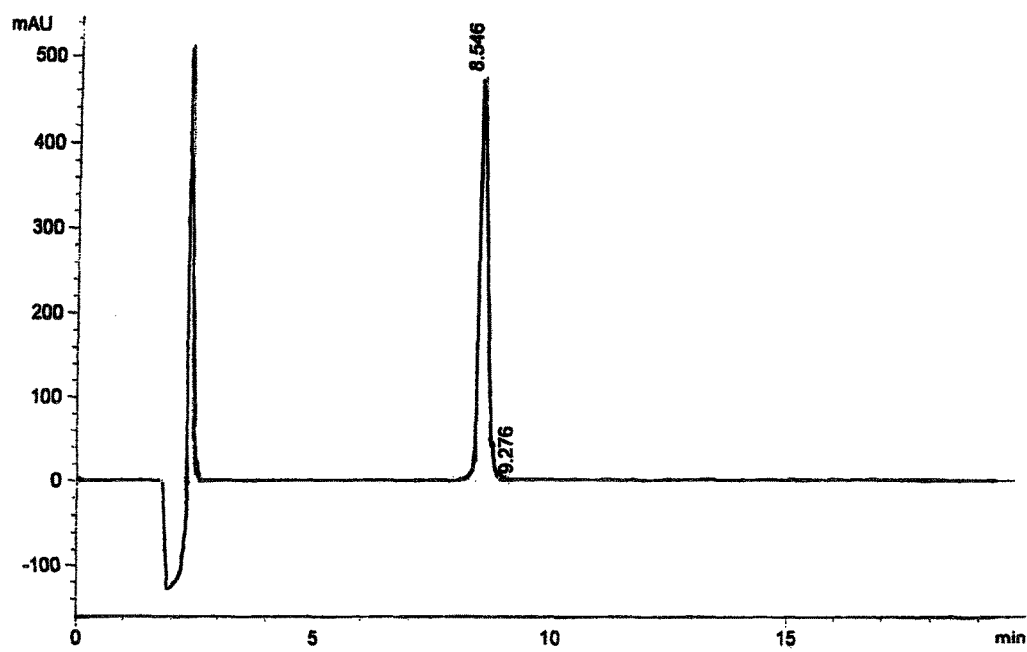
FIG. 4 shows and HPLC chromatogram of cyclic-RG CYSTEIC ACID peptide (Compound 2).
Figure 5:
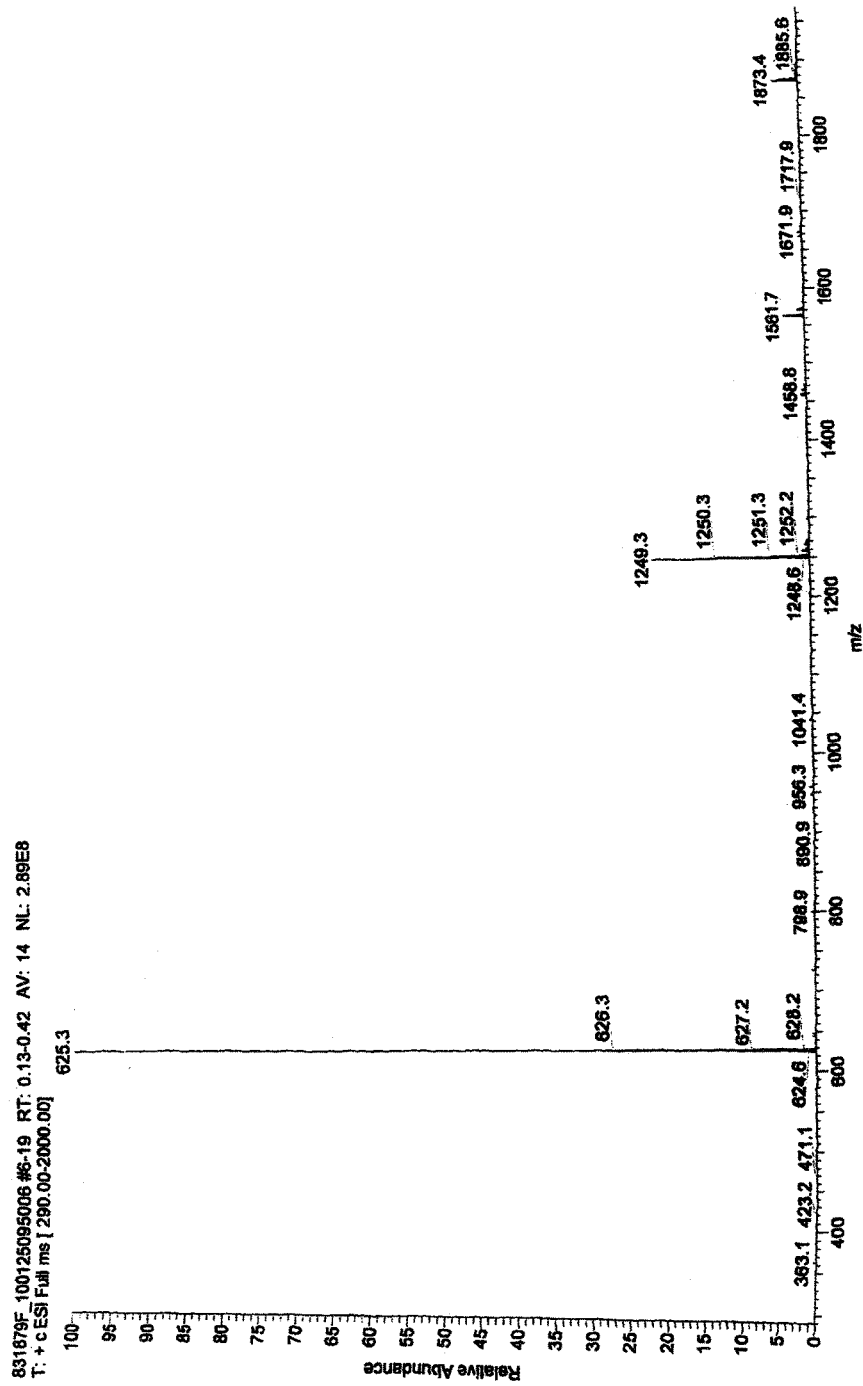
FIG. 5 shows an Electrospray mass chromatogram of cyclic-RG CYSTEIC ACID peptide (Compound 2).

A quantity of Compound 2, prepared as described above, was analyzed by High Performance Liquid Chromatography to be >99% area/area in purity (HPLC conditions: Mobile Phase A: 0.1% trifluoroacetic acid in water, B: 0.1% TFA in (80% acetonitrile plus 20% water); gradient 26% to 36% B in minutes; flow rate: 1.0 mL/minute; column: Phenomenex C18(2) 4.6×150 mm, 5μ, 100 A, detector: UV@220 nm; sample injection volume: 100.0 μL). The corresponding HPLC chromatogram is shown in FIG. 4. In addition, based on the stepwise addition of the corresponding amino acids for the synthesis of the peptide sequence, the molecular weight of purified Compound 2 was determined by Electrospray Mass Spectrometry to be 625.3 amu (theoretical mass: 625.77 amu), confirming the identity of Compound 2. The Electrospray mass spectrogram of Compound 2 is shown in FIG. 5.

Methods for Inhibiting Cellular Adhesion

The present invention also provides methods for inhibiting cellular adhesion to RGD binding sites in a human or animal subject by administering to the subject an effective amount of R-G-Cysteic Acid (i.e., linear form of R-G-NH—CH(CH$_2$—SO$_3$H)COOH or cyclic form of R-G-NH—CH(CH$_2$—SO$_3$H)COOH) or a derivative thereof (including pharmaceutically acceptable salts, hydrates, stereoisomers, multimers, cyclic forms, linear forms, drug-conjugates, pro-drugs and their derivatives).

Applicant has discovered that synthetic RG CYSTEIC ACID peptides of the present invention induce apoptosis by competitively inhibiting the cell attachment to the ECM components. Therefore, the present synthetic RG CYSTEIC ACID acid peptides and their derivatives can be used as potent integrin antagonists as therapeutic agent against angiogenesis, inflammation, cancer metastasis, thrombosis, prevention and treatment of scar formation as well as a pharmacological vitreolysis agents. In addition, in an important aspect of the present invention, an improved targeting of the α, β integrins using multimerized and radiolabeled RG CYSTEIC ACID peptides, for use as internal radiotherapeutic agents for tumor detection (diagnostic or imaging agent) and tumor treatment is envisaged. In another important aspect, improved RG CYSTEIC ACID peptide conjugates or multimeric RG CYSTEIC ACID peptide conjugates function as drug carriers, for example, as anti-cancer drug carriers for efficient tumor targeting.

As described elsewhere herein, the sulfonic acids in the RG CYSTEIC ACID peptides are stronger acids than corresponding carboxylic acids in RDG-peptides. This higher polarity of the sulfonic acid group leads to stronger intermolecular bonding. For example, R-G-Cysteic acid, which has a more polarized O—H bond, may form stronger hydrogen bonds than R-G-Aspartic acid, which has a relatively less polarized O—H bond, with the amide groups and/or side chains of the amino acids of the proteins in the integrin binding site and/or have stronger interactions with metal ions complexed in the integrin binding site. Therefore, the novel RG CYSTEIC ACID peptides and their derivatives of the present invention present improved compounds and compositions over the corresponding RGD peptides in integrin receptor recognition and binding.

Additionally, in diabetic patients with chronic hyperglycemia associated with elevated IOP, open angle glaucoma particularly is reported to be related to the accumulation of fibronectin in the trabecular meshwork tissue and the excess of fibronectin is believed to inhibit the aqueous outflow (see Oshitari, T, et al., Am. J. Ophthalmol. (2007) 143:363-365). Involvement of fibronectin in the cell-ECM interaction in the trabecular meshwork was indicated in primary open angle glaucoma (see Mark S. Filla, et al., Invest. Ophthalmol. Vis. Sci. (2002) 43:151-161; and Cheryl R. Hann, et al., Ophthalmic Res. (2001) 33: 314-324). It has also been reported that the endothelial cells of Schlemm's canal interact with extracellular matrix in influencing outflow facility (see Cindy K. Bahler et al., Invest. Ophthalmol. Vis. Sci. (2004) 45: 2246-2254). In light of the inhibition of the aqueous outflow by the presence of an excess of extracellular matrix components such as fibronectin, application of RG CYSTEIC ACID peptides and their derivatives to treat the elevated IOP of diabetic patients would be highly beneficial to diabetic patients.

The preferred RG CYSTEIC ACID peptides can be a fusion polypeptide, a cyclic or linear polypeptide, a derivatized polypeptide, including RG CYSTEIC ACID peptide derivatized or associated or coupled with drug delivery systems or other drugs, such as, for example, anti-cancer drugs, a multimerized RG CYSTEIC ACID peptide, a monoclonal antibody containing RG CYSTEIC ACID sequence that immunoreacts with integrins' binding site or functional fragment thereof.

RG CYSTEIC ACID containing polypeptides can have a sequence corresponding to the amino acid residue sequence of natural integrin adhesive binding region, such as those present in fibrinogen, fibronectin, vitronectin, von Willebrand factor, laminin, thrombospondin, and the like ligands.

The present peptide sequence consists of three amino acids having terminal guanidino, sulphonic and carboxylic groups and its derivatives coupled and/or associated with drug delivery systems, including peptide fragments, glycoproteins, and polymer groups such as PEG, Pluronic, and other polymer groups, and, liposomes and nanoparticles. Pharmaceutical compositions comprising them for treatment of various pathological disorders include injectable, gel, suspension, ointment, solid and liquid dosage forms.

Integrin receptors associated with a cell adhesion motif such as fibronectin, vitronectin, laminin, fibrinogen, thrombospondin, and von Willebrand factor, are the target epitope of RG CYSTEIC ACID peptide and its derivatives. The tripeptide, RG CYSTEIC ACID, has been discovered as a recognizable minimal amino acid sequence by cell binding domains. This sequence can also interfere with immune functions unrelated to integrins. Thus, it has been discovered that the synthetic RG CYSTEIC ACID sequence is to mimic the RGD cell binding domain, and a substitution on the α-carbon of aspartic acid gives a stronger binding affinity to the target integrins. The sulfonic acids in the RG CYSTEIC ACID-peptides are stronger acids than corresponding carboxylic acids in RDG-peptides. This higher polarity of the sulfonic acid group leads to stronger intermolecular bonding. For example, R-G-Cysteic acid, which has a more polarized O—H bond, may form stronger hydrogen bonds than R-G-Aspartic acid, which has a relatively less polarized O—H bond, with the amide groups and/or side chains of the amino acids in the integrin binding site and/or have stronger interactions with metal ions complexed in the integrin binding site.

The most general formulas for the RG CYSTEIC ACID sequences of the present invention are as follows:

Formula A:

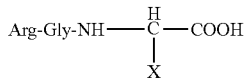

Where X=—CH(R$_1$)—S(=O)$_2$—Y;
—CH(R$_1$)—SH,
—CH(R$_1$)—OZ;
—CH(R$_1$)S(=O)Y;
—CH(R$_1$)—O—S(=O)$_2$—OX$_1$; and
—CH(R$_1$)—O—P(=O)$_2$—OX$_1$; and Wherein Y=OX$_1$, NH$_2$; X$_1$=—H, C$_1$-C$_6$ straight chain alkyl, phenyl;
R$_1$=H, C$_1$-C$_6$ straight chain alkyl, phenyl or SO$_3$H
Z=H, SO$_3$H Formula B:

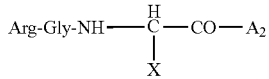

Where X=—CH(R$_1$)—S(=O)$_2$—Y;
—CH(R$_1$)—SH;
—CH(R$_1$)—OZ;
—CH(R$_1$)S(=O)Y;
—CH(R$_1$)—O—S(=O)$_2$—OX$_1$, and
—CH(R$_1$)—O—P(=O)$_2$—OX$_1$; and Wherein Y=OX$_1$, NH$_2$; X$_1$=—H, C$_1$-C$_6$ straight chain alkyl, phenyl;
R$_1$=H, C$_1$-C$_6$ straight chain alkyl, phenyl or SO$_3$H
Z=H, SO$_3$H; and
A$_2$ is selected from: -Phe-Val-Ala, -Phe-Leu-Ala, -Phe-Val-Gly, -Phe-Leu-Gly, -Phe-Pro-Gly, -Phe-Pro-Ala, -Phe-Val, or salt or N-alkylated derivative thereof. Any combination of D-form or L-form of Arg, Gly, Cysteic, Phe, Val, Ala, Leu, Pro, Thr, as well as cyclic form of the above sequence can be used.

Examples of cyclic forms include:

Formula C:

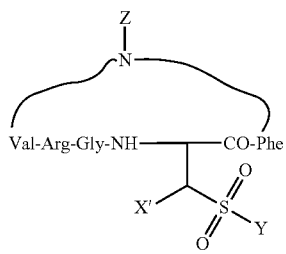

where X' is selected from: H, C$_1$-C$_6$ alkyl, Ph, SO$_3$H; Y=OH, NH$_2$ and Z=H, CH$_3$.

Cyclic forms also include penta and hepta peptides, such as for example a specific compound of General Formula C, namely, Compound 2 (Cyclo-RG CYSTEIC ACID fN(CH$_3$) V), is shown below:

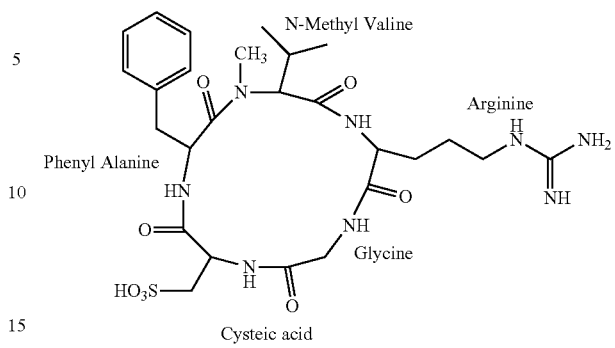

Compound 2

Formula A encompasses General Formulas I-VI described elsewhere herein. Formula B encompasses general formula VII described elsewhere herein.

$$A_1\text{-Arg-Gly-NH—CH(X)—CO-}A_2 \quad \text{Formula D:}$$

Where X=—CH(R$_1$)—S(=O)$_2$—Y;
—CH(R$_1$)—SH;
—CH(R$_1$)—OZ,
—CH(R$_1$)S(=O)Y;
—CH(R$_1$)—O—S(=O)$_2$—OX$_1$; and
—CH(R$_1$)—O—P(=O)$_2$—OX$_1$; and Wherein Y=OX$_1$, NH$_2$; X$_1$=—H, C$_1$-C$_6$ straight chain alkyl, phenyl;
R$_1$=H, C$_1$-C$_6$ straight chain alkyl, phenyl or SO$_3$H
Z=H, SO$_3$H; and
A$_1$ and A$_2$ are selected from: -Phe-Val-Ala, -Phe-Leu-Ala, -Phe-Val-Gly, -Phe-Leu-Gly, -Phe-Pro-Gly, -Phe-Pro-Ala, -Phe-Val, or salt or N-alkylated derivative thereof. Any combination of D-form or L-form of Arg, Gly, Cysteic, Phe, Val, Ala, Leu, Pro, Thr, as well as cyclic form of the above sequence can be used.

The substituted RG CYSTEIC ACID sequences includes cyclic RG CYSTEIC ACID analogues.

The application of the RG CYSTEIC ACID and its derivatives can be made subcutaneously, dermatologically, ophthamically and systemically, by employing a drug delivery system or any pharmaceutically acceptable dosage forms of injection or solid or ointment formulation.

The compounds of the present invention may be administered by any route that is suitable to bring about the intended therapeutic effect including but not limited to: oral, rectal, intravenous, intraarterial, intradermal, subcutaneous, intramuscular, intrathecal, sublingual, buccal, intranasal, transmucosal, transdermal, topical, intraocular, intravitreal, other enteral, other parenteral and/or other possible route(s) of administration.

The compounds of the present invention may be administered at any dosage that provides the intended therapeutic effect while avoiding untoward or toxic effects. Typical dosages at which the compounds of the present invention may be administered to human subjects are in the range of about 1 ng/kg to about 1.0 g/kg.

Where possible and appropriate, compounds of the present invention may optionally be prepared in the form of liposomes or nanoparticles (e.g., nanocapsules). The formation and use of liposomes is generally known to those of skill in the art. Liposomes are formed from phospholipids dispersed in an aqueous medium such that they spontaneously form multilamellar concentric bilayer vesicles sometimes referred to as multilamellar vesicles (MLVs). MLVs are typically from 25 nm to 4 μm in diameter. When sonicated, MLVs form small unilamellar vesicles (SUVs) of about 200 to 500 angstroms in diameters having cores which contain the aqueous solution. In general, when dispersed in an aqueous medium, phospholipids can form various structures other than liposomes, depending on the molar ratio of lipid to water. At low molar lipid to water ratios, liposomes will form. The physical characteristics of liposomes depend on pH, tonicity and the presence or non-presence of divalent cations. Liposomes can interact with cells by different mechanisms, including 1) endocytosis (e.g., phagocytosis of the liposome by cells such as macrophages and neutrophils), adsorption to the cell surface, 2) interaction with cell-surface components, 3) fusion with the plasma cell membrane by insertion of the lipid bilayer of the liposome into the plasma membrane or 4) transfer of liposomal lipids to cellular or subcellular membranes, or vice versa. Varying the liposome formulation can alter which mechanism(s) by which the liposomes will interact with cells in the paranasal sinus, nasal mucosa, etc.

A nanocapsule is any nanoparticle that consists of a shell and a space, in which desired substances may be placed. Techniques for forming nanocapsules are known in the art. Polymeric nanocapsules can be made in specific sizes and shapes. They can be produced as monodisperse particles which have precisely defined physical and chemical properties and, thus, can be tailored to facilitate release of the therapeutic or diagnostic substance in response to particular bimolecular triggering mechanisms, such as pH, mucous flow or other conditions present within the paranasal sinus or other area in the ear, nose or throat where the device is implanted. Nanocapsules can be used in the present invention as "smart drugs" which have specific chemical receptors or binding sites that will bind to specific target cells (e.g., cancer cells or cells associated with inflammatory conditions.

The following are non-limiting examples of formulations for pharmaceutical preparations containing compounds of the present invention. Also included are examples of the safety and/or efficacy demonstrated using exemplary RG CYSTEIC ACID peptides or derivatives in inhibiting cell adhesion. As may be used herein, the terms "RG CYSTEIC ACID Peptide," "RGCysteic Acid peptide", "RGC" and "RGCys-peptide" and "compounds of the present invention" shall synonymously mean compositions containing the sequence R-G-Cysteic Acid and their derivatives, including but not limited to those defined by General Formulas I-VII and Compounds 1, and 3-5 as described herein.
Methods for Targeted Integrin Receptor Therapy for Treatment of Eye Diseases Included among the numerous potential therapeutic uses of the compositions of the present invention is the treatment of certain disorders of the eye characterized by excessive vascularization of the retina (herein generally referred to as "neovascular eye disease." The following non-limiting examples discuss uses of the compositions of the present invention alone, and in combination with other agents, to treat such neovascular eye disorders.

If and when used in this patent application, the following acromyms and abbreviations shall have the following meanings:
AE Adverse Event
Allegro Allegro Ophthalmics, LLC
AMD Age-Related Macular Degeneration
BCVA Best corrected visual acuity
CNV Choroidal Neovascularization
CRA Clinical Research Associate
DME Diabetic Macular Edema
DR Diabetic Retinopathy
Dry AMD Dry Age-Related Macular Degeneration
ERG Electroretinography
ETDRS Early Treatment Diabetic Retinopathy Study
FDA Food and Drug Administration
GCP Good Clinical Practice
IOP Intraocular Pressure/Tonometry
IRB Institutional Review Board
OCT Optical Coherence Tomography
OD Right eye
OS Left eye
PI Principal Investigator
PDR Proliferative Diabetic Retinopathy
PVD Posterior Vitreous Detachment
RVO Retinal Vein Occlusion
SAE Serious Adverse Event
SC Study Coordinator
USP United States Pharmacopeia
VEGF Vascular Endothelial Growth Factor
Wet AMD Wet Age-Related Macular Degeneration Age-related macular degeneration (AMD) is the leading cause of blindness in the Western world, and patients with this condition suffer irreversible damage to the macula, or central part of the retina. Dry AMD causes slowly progressive visual loss, while Wet AMD can lead to rapid deterioration of central vision. Wet AMD causes the vast majority of severe vision loss in affected patients, but both forms represent a major public health concern for the $21^{st}$ century. Approximately 1.5 million Americans have choroidal neovascularization (CNV) secondary to AMD, and each year 200,000 new cases develop. It has been documented that the prevalence, incidence, and rates of progression of AMD all increase with age. In the United States, people over the age of 65 make up one of the largest segments of the population, and this demographic category is projected to increase substantially over the coming decades. The population over the age of 85 in the United States is expected to double by 2020. Thus, AMD represents a significant public health problem for the United States. In particular, Wet AMD is the most significant factor causing poor vision in patients with AMD. Wet AMD is characterized by choroidal angiogenesis, i.e., the development of abnormal blood vessels under the retina. These vessels leak fluid, bleed, and transform into fibrovascular scar tissue. This process disrupts the overlying photoreceptors and causes severe visual loss. There is good evidence that diminished choroidal perfusion leads to retinal pigment epithelial (RPE) dysfunction and photoreceptor loss in AMD. Diabetic macular edema (DME) is the result of thickening of the center part of the retina due to damage of retinal capillaries from diabetes. DME is the leading cause of blindness in the working age population, also causing mild to moderate vision impairment in this population as well as people who no longer may be working. Application of laser to damaged capillaries within thickened retina has been the mainstay of treatment for over 25 years. Recent results from the Diabetic Retinopathy Clinical Research Network demonstrated that in eyes with reduced visual acuity from DME involving the center of the macula, anti-VEGF therapy with Lucentis in combination with focal/grid laser, provides superior vision outcomes and an acceptable safety profile compared with the previous standard treatment of laser alone. The molecular events involved in the development of pre-retinal and choroidal neovascularization have not been fully elucidated; however, vascular endothelial growth factor (VEGF) has been shown to play a major role in the process. Integrins $\alpha_5\beta_1$, $\alpha_v\beta_3$ and $\alpha_v\beta_5$ are also implicated in the angiogenic process, and are known to be expressed in neovascular ocular tissue from patients with Wet AMD and PDR. There are also a number of other molecules that play important roles: bFGF, IL-8, PDGF, various proteases including plasminogen activator and matrix metalloproteinases, chemokines and other inflammatory mediators. Endothelial cell proliferation, increased vascular permeability, inflammation, and excessive production of VEGF are some of the major pathological developments in Wet AMD and DME.

The present invention provides a new class of therapeutic drugs for retinal vascular diseases, including Wet AMD, DR and DME. The compounds of the present invention have multiple mechanisms of action against retinal vascular diseases including a) causing anti-angiogenesis by inhibiting VEGF production directly, b) causing inhibition of the VEGF-2 receptor, c) causing down regulation or inhibition of tyrosine kinase and d) causing liquefaction of the vitreous body and posterior vitreous detachment thereby allowing VEGF diffusion out of the eye. The mechanisms of action may be employed alone (e.g., by therapy using only compound(s) of the present invention) or may be additive or complementary inhibition of existing VEGF (e.g., by combination therapy using compound(s) of the present invention in combination with a composition that binds, traps, scavenges or otherwise deters the effect of VEGF that has already been produced, examples of which include but are not necessarily limited to: Avastin, Lucentis and/or Eylea). Avastin (bevacizumab) is an anti-VEGF monoclonal antibody. Lucentis (ranibizumab) is a recombinant humanized IgG1 kappa isotype monoclonal antibody fragment. Eylea (aflibercept) is a recombinant fusion protein consisting of portions of human. Vascular endothelial growth (VEGF) receptors 1 and 2.

Figure 6:
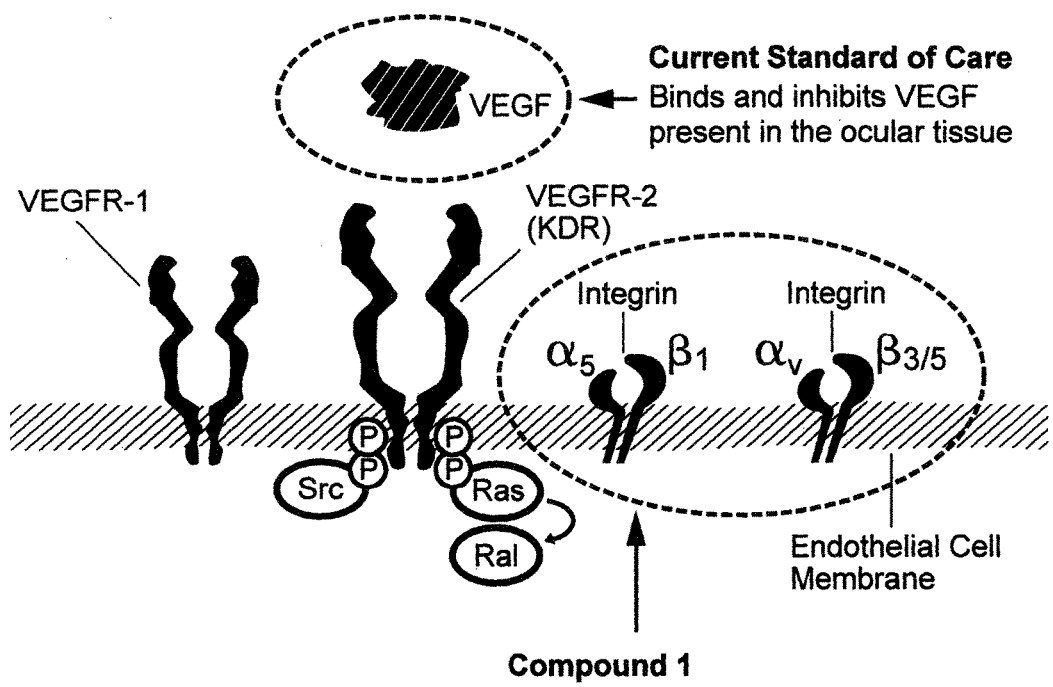
FIG. 6 is a schematic diagram illustrating the mechanism of action of the compounds of the present invention.
Figure 7A:
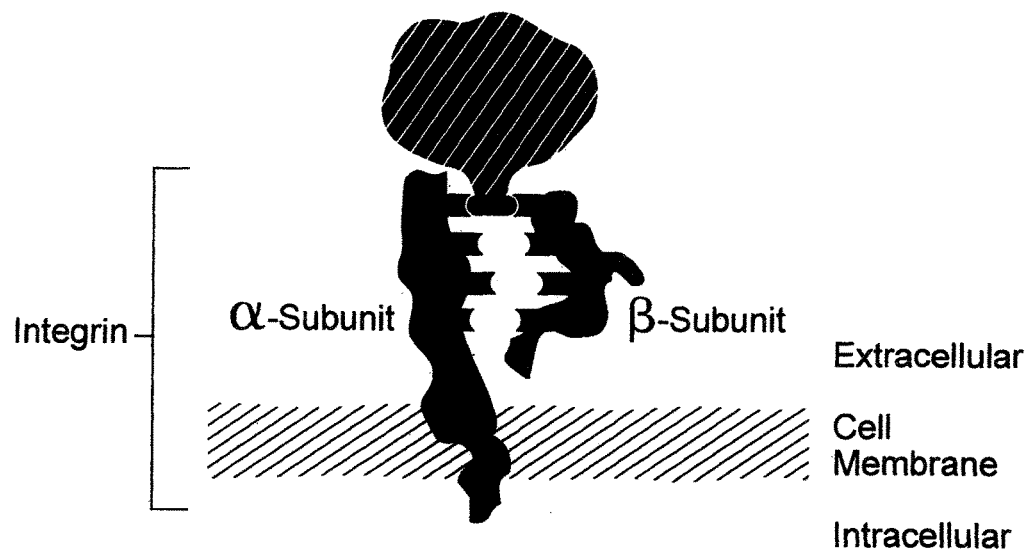
FIG. 7A and FIG. 7B are schematic diagrams further illustrating the mechanism of action of compositions of the present invention.
Figure 7B:
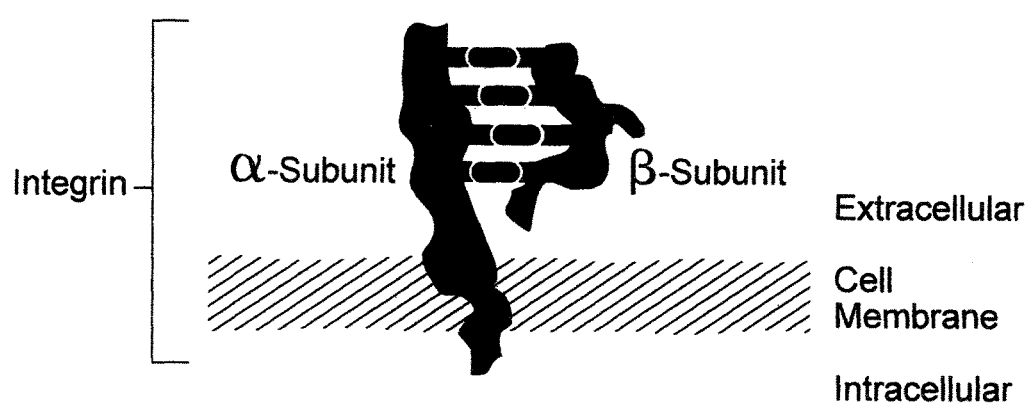

By down-regulating VEGF production rather than sequestering pre-existing VEGF supply, the compounds of the present invention have unique mechanisms of action that allow intervention much earlier in the angiogenic cascade as compared to the current standard of care. This is illustrated schematically in FIG. 6. In addition to working at a much earlier stage of the angiogenic cascade, the compounds of the present invention bind to multiple integrin sub-units, as opposed to monoclonal antibody approaches that are 500 times larger and specific to only one integrin subunit as shown in FIG. 7A. In contrast, an oligopeptide is able to bind much more effectively to multiple integrin sub-units involved in angiogenesis, as shown in FIG. 7B.

Examples of neovascular eye diseases that can potentially be treated with compounds of the present invention include Diabetic Retinopathy (DR), Diabetic Macular Edema (DME) and Age-Related Macular Degeneration (AMD). The currently available pharmaceutical treatments for these disorders include certain drugs that bind, trap, scavenge or otherwise deter the effect of VEGF that has already been produced (referred to generally herein as VEGF Traps). Commercially available examples of such "VEGF traps" include bevacizumab (Avastin), ranibizumab (Lucentis) and aflibercept (Eylea). Bevacizumab is described as an anti-VEGF monoclonal antibody. Ranibizumab is described as a recombinant humanized IgG1 kappa isotype monoclonal antibody fragment. Aflibercept is described as a recombinant fusion protein consisting of portions of human vascular endothelial growth (VEGF) receptors 1 and 2. These anti-VEGF antibody-based treatments are typically administered by repeated intravitreal injections, at 4 to 6 week intervals, potentially indefinitely, and at substantial inconvenience, cost and cumulative risk of infection.

Unlike the existing VEGF Traps, the compositions of the present invention have multiple mechanisms of action against neovascular eye diseases, specifically: anti-angiogenesis by directly inhibiting VEGF production, inhibition of the VEGF-2 receptor, down regulation of tyrosine kinase, and inducement of vitreal liquefaction and posterior vitreous detachment (which facilitates diffusion of VEGF or other deleterious entities away from the retina and out of the eye). Some of the examples set forth below describe uses of Compound 1 alone and in combination with other agents (VEGF Traps) in the treatment of neovascular eye diseases.

It is to be appreciated that, in addition to the treatment of neovascular eye diseases, the compositions of the present invention are also useable to treat various other eye disorders which do or do not cause retinal neovascularization. Examples of eye disorders which may be treated by compositions of the present invention include but are not necessarily limited to wet age-related macular degeneration, diabetic macular edema, proliferative or non-proliferative diabetic retinopathy, liquefaction of the vitreous humor, induction of posterior vitreo-retinal detachment (PVD), pathogenesis of vitreoretinal diseases, such as idiopathic macular hole, vitreomacular traction, age related macular degeneration, choroidal neovascularization, vitreoretinal surgery, vein occlusion, corneal neovascularization, ischemic optic nerve, rubiosis iridis and prevention of scar formation in glaucoma surgery.

Pharmaceutical Formulations

The following are examples of pharmaceutical formulations I-X, which contain R-G-Cysteic Acid Peptides of the present invention, such as any of those defined by General Formulas I-VII or any of Compounds 1-5 as described herein.

| Formulation I | |
|---|---|
| R-G-Cysteic Acid Peptide (RGCys-peptide) | 0.0001 mg to 10 g |
| NaCl | 0.01 mg to 0.9 g |
| Water | QS to 100.0 mL |
| Formulation II | |
| RGCysteic Acid Peptide (RGCys-peptide) | 0.0001 mg to 10 g |
| EDTA | 0.001 mg to 100 mg |
| NaCl | 0.01 mg to 0.9 g |
| Water | QS to 100.0 mL |
| Formulation III | |
| RGCysteic-peptide | 0.0001 mg to 10 g |
| EDTA | 0.001 mg to 100 mg |
| NaCl | 0.01 mg to 0.9 g |
| Citric Acid | 0.0001 mg to 500 mg |
| Water | QS to 100.0 mL |
| Formulation IV | |
| RGCysteic-peptide | 0.0001 mg to 10 g |
| NaCl | 0.01 mg to 0.9 g |
| Phosphate Buffer to | pH = 3.0-9.0 |
| Water | QS to 100.0 mL |
| Formulation V | |
| RGCysteic-peptide | 0.0001 mg to 10 g |
| EDTA | 0.001 mg to 100 mg |
| NaCl | 0.01 mg to 0.9 g |
| Phosphate Buffer to | pH = 3.0-9.0 |
| Water | QS to 100.0 mL |
| Formulation VI | |
| RGCysteic-peptide | 0.0001 mg to 10 g |
| NaCl | 0.01 mg to 0.9 g |
| Borate Buffer to | pH = 3.0-9.0 |
| Water | QS to 100.0 mL |

-continued

Formulation VII

| | |
|---|---|
| RGCysteic-peptide | 0.0001 mg to 10 g |
| Hyaluronic Acid Sodium salt | 0.01 to 10% |
| Boric Acid | 0.01 to 1.0% |
| Polyethyleneglycol (PEG 8000) | 0.01 to 10% |
| Sodium Chloride | 0.10 to 0.9% |
| Potassium Chloride | 0.01 to 0.20% |
| Calcium Chloride Dihydrate | 0.001 to 0.05% |
| Magnesium Chloride Hexahydrate | 0.01 to 0.20% |
| Preservative | |
| pH | 4.0-8.0 |
| Water | QS to 100.0 mL |

Formulation VIII

| | |
|---|---|
| RGCysteic-peptide | 0.0001 mg to 10 g |
| Hyaluronic Acid Sodium salt | 0.01 to 10% |
| Carboxymethyl Cellulose | 0.01 t0 10% |
| Boric Acid | 0.01 to 1.0% |
| Polyethyleneglycol (PEG 8000) | 0.01 to 10% |
| Sodium Chloride | 0.10 to 0.9% |
| Potassium Chloride | 0.01 to 0.20% |
| Calcium Chloride Dihydrate | 0.001 to 0.05% |
| Magnesium Chloride Hexahydrate | 0.01 to 0.20% |
| Preservative | |
| pH | 4.0-8.0 |
| Water | QS to 100.0 mL |

Formulation IX

| | |
|---|---|
| RGCysteic-peptide | 0.0001 mg to 10 g |
| Hyaluronic Acid Sodium salt | 0.01 to 10% |
| Sodium Alginate | 0.01 t0 10% |
| Boric Acid | 0.01 to 1.0% |
| Polyethyleneglycol (PEG 8000) | 0.01 to 10% |
| Sodium Chloride | 0.10 to 0.9% |
| Potassium Chloride | 0.01 to 0.20% |
| Calcium Chloride Dihydrate | 0.001 to 0.05% |
| Magnesium Chloride Hexahydrate | 0.01 to 0.20% |
| Preservative | |
| pH | 3.0-8.0 |
| Water | QS to 100.0 mL |

Formulation X

| | |
|---|---|
| RGCysteic-peptide | 0.0001 mg to 10 g |
| Hyaluronic Acid Sodium salt | 0.01 to 10% |
| Alginic Acid | 0.01 t0 10% |
| Boric Acid | 0.01 to 1.0% |
| Polyethyleneglycol (PEG 8000) | 0.01 to 10% |
| Sodium Chloride | 0.10 to 0.9% |
| Potassium Chloride | 0.01 to 0.20% |
| Calcium Chloride Dihydrate | 0.001 to 0.05% |
| Magnesium Chloride Hexahydrate | 0.01 to 0.20% |
| Preservative | |
| pH | 3.0-8.0 |
| Water | QS to 100.0 mL |

Comparison of The PVD-Inducing Effects of RGD Peptides and Glycyl-Arginyl-Glycyl-Cysteic-Threonyl-Proline-COOH (GRG Cysteic Acid TP; Compound 1) in Rabbits In this example, the PVD-Inducing Effects of RGD Peptides and Glycyl-Arginyl-Glycyl-Cysteic-Threonyl-Proline-COOH (RG Cysteic Acid Peptide; GRG Cysteic Acid TP; Compound 1) were compared in rabbits. The protocol for this study was as follows:

Protocol:
Animal Model
a) 20 Male and Female Rabbits
b) Weighing approximately 1.5-2.5 kg.
c) Divide into 2 groups
i) 10 Rabbits were injected Intravitreally with 2.5% RGD solution at pH=6.5
 a) 10 Right Eye injected with 2.5% RGD solution
 b) 5 Left Eye used as BSS Control
 c) 5 Left Eyes injected with 2.5% RGD+0.02% EDTA at pH=6.5
ii) 10 Rabbits were injected Intravitreally with 2.5% RGCysteic solution at pH=6.5
 a) 10 Right Eye injected with 2.5% RGCysteic solution at pH=6.5
 b) 10 Left Eye injected with 2.5% RGCysteic solution+ 0.02% EDTA at pH=6.5

Active Chemicals
d) Sodium EDTA—99.0-100.5% from Spectrum Chemical Corp.
e) RG Cysteic Acid—cGMP supplier (Purity >98%).
f) RGD—cGMP supplier (Purity >98%).
g) BSS solution Both the RG Cysteic Acid, RGD, RG Cysteic Acid+Sodium EDTA, RGD+Sodium EDTA, and the BSS solutions were injected into the vitreous cavity 24 hours prior to surgery. The rabbits (10 mg/kg body weight) were anesthetized with an intramuscular injection of 2.0 ml of 1:1 combination of xylazine (100 mg/ml) and Ketamine hydrochloride (100 mg/ml). Pupils are dilated with topical cyclopentolate hydrochloride 1% and Phenylephrine hydrochloride 10%.

All animals were initially examined with slit lamp biomicroscopy and indirect ophthalmoscopy to exclude any animals with pre-existing vitreoretinal abnormalities. The intravitreal injection of 0.10 cc was administered 2 mm posterior to the limbus in the supranasal quadrant using a 30-gauge needle attached to a 1.0 cc syringe. Care must be taken to avoid damage to the lens or retina.

Twenty four hours following injection and immediately before initiation of a mechanical vitrectomy, a B-scan ultrasonography was performed to determine the status of the posterior vitreous and also the liquefaction of the vitreous. A two-port pars plana vitrectomy was performed using an infusion fiberoptic and a vitreous cutter attached to a vitrectomy unit. Following a 30 second core vitrectomy, the vitreous cutter was directed to the peripapillary retinal surface where, using low aspiration (<30 mmHg) a separation of the posterior cortical vitreous from the retinal surface was attempted in 4 quadrants. The sclerotomies were sutured and a postoperative B-Scan ultrasonography was carried out to determine the presence and extent of any PVD present in each quadrant. The animals were euthanized with intracardiac sodium pentobarbital injections, and the eyes were immediately enucleated.

Classification of Liquefaction of the Vitreous and PVD was graded following this grading system to evaluate the extent of PVD based on the postoperative B-Scan ultrasound examination;
 Grade 0. a) No detachment of the posterior Vitreous is observed.
  b) Vitreous Liquefaction
 Grade 1. a) Consists of eyes in which the vitreous is detached in 2 or less quadrants.
  b) Vitreous Liquefaction
 Grade 2. a) Consists of eyes in which the vitreous is detached in 3 or more quadrants, but with remaining focal attachments along the medullary rays
  b) Vitreous Liquefaction
 Grade 3. a) Consists of eyes in which the vitreous is totally detached from the retinal surface
  b) Vitreous Liquefaction All eyes underwent a sharp razor penetration at the superior pole sub-adjacent to the pars plana immediately after enucleating to insure rapid penetration of fixative. Care was taken to avoid damage to the adjacent retina and lens. The eyes were immersed in 2% paraformaldehyde plus 2.5% glutaraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope.

Results:
Injection: 2.5% RG Cysteic Acid
Group 1. At Baseline all Animals have no PVD in both eyes

| Eye Examined | Animal 1 | Animal 2 | Animal 3 | Animal 4 | Animal 5 |
|---|---|---|---|---|---|
| O D Treated | Grade 3-4 Q Vitreous totally Detached | Grade 3-4 Q Vitreous totally Detached | Grade 2-3 Q Vitreous detached in 3 or more Q | Grade 3-4 Q Vitreous totally Detached | Grade 1-2 Q Vitreous detached in 2 or less Q |
| O S Control | Grade 0 | Grade 0 | Grade 0 | Grade 0 | Grade 0 |

Injection: 2.5% of RGD
Group 2. At Baseline all Animals have no PVD in both eyes

| Eye Examined | Animal 1 | Animal 2 | Animal 3 | Animal 4 | Animal 5 |
|---|---|---|---|---|---|
| O D Treated | Grade 3-4 Q Vitreous totally Detached | Grade 2-3 Q Vitreous detached in 3 or more Q | Grade 1-2 Q Vitreous detached in 2 or less Q | Grade 3-4 Q Vitreous totally Detached | Grade 3-4 Q Vitreous totally Detached |
| O S Control | Grade 0 | Grade 1-2 Q Vitreous detached in 2 or less Q | Grade 3-4 Q Vitreous totally Detached | Grade 1-2 Q Vitreous detached in 2 or less Q | Grade 0 |

Injection: 2.5% RG Cysteic Acid+0.02% NaEDTA
Group 3. At Baseline all animals have no PVD in both eyes

| Eye Examined | Animal 1 | Animal 2 | Animal 3 | Animal 4 | Animal 5 |
|---|---|---|---|---|---|
| O D Treated | Grade 1-2 Q Vitreous detached in 2 or less Q | Grade 3-4 Q Vitreous totally Detached | — | Grade 3-4 Q Vitreous totally Detached | Grade 1-2 Q Vitreous detached in 2 or less Q |
| O S Control | Grade 1-2 Q Vitreous detached in 2 or less Q | Grade 0 | — | Grade 2-3 Q Vitreous detached in 3 or more Q | Grade 0 |

Injection: 2.5% RGD+0.02% NaEDTA
Group 4. At Baseline all animals have no PVD in both eyes

| Eye Examined | Animal 1 | Animal 2 | Animal 3 | Animal 4 | Animal 5 |
|---|---|---|---|---|---|
| O D Treated | Grade 3-4 Q Vitreous totally Detached | Grade 0 | Grade 3-4 Q Vitreous totally Detached | Grade 0 | Grade 1-2 Q Vitreous detached in 2 or less Q |
| O S Control | Grade 2-3 Q Vitreous detached in 3 or more Q | Grade 2-3 Q Vitreous detached in 3 or more Q | Grade 0 | Grade 0 | Grade 0 |

The results of this study show that RGD and RG Cysteic Acid (GRG Cysteic Acid TP; Compound 1) have similar properties and injection of 2.5% RG Cysteic Acid intravitreally causes complete separation of the vitreous from the retina in 24 hours, and in addition the vitreous of both the RGD and the RG Cysteic Acid rabbits are completely liquefied.

Over all, the activity of RG Cysteic Acid is equal or slightly better than that of RGD in inducing complete PVD in the rabbits and liquefying the vitreous. This is possibly due to its stronger competitive binding ability to the binding sites of integrin-extracellular matrix interactions than RGD. As described elsewhere herein, sulfonic acids are stronger acids than corresponding carboxylic acids. This higher polarity of the sulfonic acid group leads to stronger intermolecular bonding. For example, R-G-Cysteic acid, which has a more polarized O—H bond, may form stronger hydrogen bonds than R-G-Aspartic acid, which has a relatively less polarized O—H bond, with the amide groups and/or side chains of the amino acids in the integrin binding site and/or have stronger interactions with metal ions complexed in the integrin binding site.

The results also indicate that when these compounds are administered with 0.02% Sodium Edetate, the activity of both RGD as well as RG Cysteic Acid are not altered.

The results also show that there were no adverse effects or adverse safety effects from the intravitreal injection of the RG Cysteic Acid compound Compound 1 or the RGD compound.

Safety Study of Multiple Injections of RGCysteic Acid Peptide Compound 1 (GRG Cysteic Acid TP) in Rabbit Eyes In this example, multiple injections of RGCysteic Acid Peptide Compound 1 were administered to the eyes of 5 Male and 4 Female New Zealand Rabbits weighing approximately 1.5-2.5 kg. and the eyes were examined as described in the following paragraphs.

The study then protocol was as follows:
A) Baseline Examinations: At baseline the right and the left eyes of all 9 rabbits were examined slit lamp biomicroscopy and indirect ophthalmoscopy to confirm that no animals had pre-existing vitreoretinal abnormalities. In addition β-scan ultrasonography as well as ERG scans were performed on the left and right eyes of all 9 animals to obtain baseline readings.
B) Experimental Treatments: All 9 Rabbits then received intravitreal injections of either solution or saline (control). The treatment solutions were prepared as follows:
RGCysteic Acid Solution: a 2.5 mg/100 µl solution of RGCysteic Acid (Compound 1) containing 0.02 mg of disodium EDTA+ 0.80 mg of sodium chloride and USP sterile Water for injection having a pH adjusted to 6.5.

Saline (control): a USP Isotonic sterile saline solution having an adjusted pH of 6.5.

The dosing proceeded as follows:

1) The right eye of each of the 9 rabbits was injected intravitreally with 100 of the 2.5 mg/100 µl RGCysteic Acid Solution (delivering a dose=2.5 mg of Compound 1)

2) The Left eye of each of the 9 rabbits was injected intravitreally with 100 µl of the Saline (control).

3) One day after the initial intravitreal injections, the right and the left eyes of all 9 Rabbits were examined, by slit lamp biomicroscopy and indirect ophthalmoscopy to check if any of the rabbits have any adverse effects from the injection.

4) On the $7^{th}$ day after the $1^{st}$ injections, the right and the left eyes of all 9 Rabbits were again examined by slit lamp biomicroscopy and indirect ophthalmoscopy to determine if any of the rabbits exhibited adverse effects from the injection. In addition ERG scan were performed on all right and left eyes of all the animals to determine if there were any changes from baseline 5) A group of 3 rabbits, numbers 901, 904 and 909, was then randomly selected and mechanical vitrectomy was performed on the right and left eyes of those 3 selected animals to determine the status of the posterior vitreous.

6) The 3 randomly selected animals, numbers 901, 904 and 909, were euthanized with intracardiac sodium pentobarbital injections, and the eyes were immediately enucleated. All eyes underwent a sharp razor penetration at the superior pole sub-adjacent to the pars plana immediately after enucleation to insure rapid penetration of fixative. Care was taken to avoid damage to the adjacent retina and lens. The eyes were immersed in 2% paraformaldehyde plus 2.5% gluteraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope. The other samples were subjected to Histopathological examination.

The remaining 6 Rabbits, numbers 902, 903, 905, 906, 907 and 908 were injected a second time 7 days post first injection.

1) The right eye of each of the 6 remaining rabbits was again injected intravitreally with 100 of the 2.5 mg/100 µl RGCysteic Acid Solution (delivering a second 2.5 mg dose of Compound 1)

2) The left eye of each of the 6 remaining rabbits was again injected intravitreally with 100 µl of the Saline (control).

3) One day after the $2^{nd}$ intravitreal injections, the right and the left eyes of all 6 remaining rabbits were examined by slit lamp biomicroscopy and indirect ophthalmoscopy to check if any of the rabbits have any adverse effects from the injection.

4) On the $7^{th}$ day after the $2^{nd}$ injections, the right and the left eyes of all 6 reaming rabbits were examined, by slit lamp biomicroscopy and indirect ophthalmoscopy to check for any adverse effects from the injections. In addition ERG scans of the left and right eyes of all the animals were run to determine if there were any changes from the baseline.

5) Three rabbits, numbers 902, 903, and 907, were then randomly selected from the remaining 6 animals and mechanical vitrectomy was performed on the right and left eyes of those 3 randomly selected animals to determine the status of the posterior vitreous.

6) The 3 randomly selected animals, numbers 902, 903, and 907 were then euthanized with intracardiac sodium pentobarbital injections, and the eyes were immediately enucleated. All eyes underwent a sharp razor penetration at the superior pole sub-adjacent to the pars plana immediately after enucleation to insure rapid penetration of fixative. Care was taken to avoid damage to the adjacent retina and lens. The eyes were immersed in 2% paraformaldehyde plus 2.5% gluteraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope. The other samples were subjected to Histopathological examination.

The remaining group of 3 Rabbits, numbers 905, 906, and 908, were then injected a third time, 14 days after the first injection, as follows:

1) The right eye of each of the 3 remaining rabbits was again injected intravitreally with 100 of the 2.5 mg/100 µl RGCysteic Acid Solution (delivering a third 2.5 mg dose of Compound 1)

2) The left eye of each of the 3 remaining rabbits was again injected intravitreally with 100 µl of the Saline (control).

3) One day after the $3^{rd}$ intravitreal injections, the right and the left eyes of all 6 remaining rabbits were examined, by slit lamp, biomicroscopy and indirect ophthalmoscopy to check if any of the rabbits have any adverse effects from the injection.

4) On the $7^{th}$ day after the $3^{rd}$ injections, the right and the left eyes of all 3 remaining rabbits were again examined by slit lamp biomicroscopy and indirect ophthalmoscopy to check for any adverse effects from the injections. In addition ERG scans of the left and right eyes of all the animals were run to determine if there were any changes from the baseline.

5) Mechanical vitrectomy was performed on the right and left eyes of the 3 remaining animals (Nos. 905, 906 and 908) to determine the status of the posterior vitreous.

6) The 3 remaining animals (Nos. 905, 906, and 908) were euthanized with intracardiac sodium pentobarbital injections, and the eyes were immediately enucleated. All eyes underwent a sharp razor penetration at the superior pole sub-adjacent to the pars plana immediately after enucleation to insure rapid penetration of fixative. Care was taken to avoid damage to the adjacent retina and lens. The eyes were immersed in 2% paraformaldehyde plus 2.5% gluteraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope. The other samples were subjected to Histopathological examination.

3) Active Chemicals

The active chemicals used in this study were as follows:

a. Disodium EDTA—99.0-100.5% from Spectrum Chemical Corp.

b. RGCysteic Acid Peptide (Compound 1)

c. USP sterile isotonic saline solution

4) Study Formulations a) RGCysteic Acid Solution: 2.5 mg/100 µl solution of RGCysteic Acid containing 0.02 mg of disodium EDTA+ 0.80 mg of sodium chloride and USP sterile water for injection adjusted to a pH=6.5. Sterile filter through a 0.22µ filter into a 2.0 mL vial.

b) Saline (Control): USP Isotonic sterile saline solution pH adjusted 6.5. Sterile filtered through a 0.22µ filter into a sterile vial.

5) Anesthesia for Injection Preparation
   a. Intramuscular injection of 2.0 mL of a 1:1 combination of xylazine (100 mg/ml) and Ketamine hydrochloride (100 mg/ml)
   b. Pupils were dilated with topical cyclopentolate hydrochloride 1% and Phenylephrine hydrochloride 10%

6) Intravitreal Injection Preparation:
A sterile vial containing the RGCysteic Acid solution containing 2.5 mg/100 µl and isotonic sterile saline solution, pH adjusted to 6.5 was provided.

Prior to the injection, the investigator confirmed that there was 0.10 cc (100 micro liters) of solution in the 1.0 cc syringe.

7) Injection Procedure:
Since the intravitreal injections do not result in a level of visual disability sufficient to disrupt the normal daily activity of the rabbits, this is not considered a major survival procedure according to the animal resolution of the Association for Research in Vision and Ophthalmology guidelines.

Both the RGCysteic Acid solution as well as the sterile saline solutions was injected into the vitreous cavity after the baseline examination of slit lamp Biomicroscopy, Ophthalmoscopy and ERG was completed on the Rabbits. The Rabbits (10 mg/kg body weight) were anesthetized with an intramuscular injection of 2.0 ml of 1:1 combination of xylazine (100 mg/ml) and Ketamine hydrochloride (100 mg/ml). Pupils were dilated with topical cyclopentolate hydrochloride 1% and Phenylephrine hydrochloride 10%.

All animals were initially examined with slit lamp biomicroscopy and indirect opthalmoscopy to exclude any animals with pre-existing vitreoretinal abnormalities. The intravitreal injection of 0.10 cc was administered 2 mm posterior to the limbus in the supronasal quadrant using a 30-gauge needle attached to a 1.0 cc syringe. Care was taken to avoid damage to the lens or retina.

Seven (7) days following injection a mechanical Vitrectomy was performed on the animals. A two-port pars plana vitrectomy was performed using an infusion fiberoptic and a vitreous cutter attached to a vitrectomy unit. Following a 30 second core vitrectomy, the vitreous cutter was directed to the peripapillary retinal surface where, using low aspiration (<30 mmHg) a separation of the posterior cortical vitreous from the retinal surface was attempted in 4 quadrants. The animals were euthanized with intracardiac sodium pentobarbital injections, and the eyes were immediately enucleated.

All eyes underwent a sharp razor penetration at the superior pole sub-adjacent to the pars plana immediately after enucleation to insure rapid penetration of fixative. Care was taken to avoid damage to the adjacent retina and lens. The eyes were immersed in 2% paraformaldehyde plus 2.5% gluteraldehyde for a minimum of 24 hours at 4 degrees Celsius. A unique posterior calotte was removed, dehydrated in methanol, and dried in carbon dioxide to the critical point, sputter-coated in gold and photographed using the scanning electron microscope.

Analysis of Results
The data on the Safety between eyes treated with RGCysteic Acid solution and sterile saline solution was analyzed for safety using the following techniques:
   i) Slit lamp biomicroscopy;
   ii) Ophthalmoscopy;
   iii) ERG;
   iv) Histopathology; and
   v) Electron microscopy.

Safety Profile:
First Intravitreal administration of 100 µl of 2.5% RGCysteic Acid solution to the group of nine Rabbits numbers 901, 902, 903, 904, 905, 906, 907, 908, 909, was not associated with any significant toxicity at all time points. There was no significant difference in reported adverse effects between the 2.5% RGCysteic Acid group and the isotonic saline solution group. This lack of toxicity was determined by clinical examination, indirect ophthalmoscopy and ultrasound β-scan and mechanical vitrectomy.

Slit lamp biomicroscopy was performed at all study visits and focused on the lids, conjunctiva and sclera, cornea, endothelial changes, anterior chamber reaction, iris, lens and capsule, as well as the anterior vitreous for signs for inflammation demonstrate a near complete lack of inflammatory reaction to intravitreal injections of 100 µl of 2.5% RGCysteic Acid solution and the isotonic saline solution group. At all study points and in all study groups there did not appear to be any signs of significant toxicity induced by the test articles.

Clinical evaluation of the posterior segment was also followed throughout the study to ensure that there was no significant retinal toxicity present. Indirect ophthalmoscopy as well as slit lamp fundus evaluations were carried out at each evaluation time point with specific attention to any signs of retinal toxicity. The posterior segment was evaluated for any changes in vitreous density, vitreous liquefaction, vitreous attachment, and possible hemorrhage. The retina was evaluated for any signs of RPE toxicity, retinal vascular compromise retinal hemorrhage, exudates, retinal tears, breaks, or detachments. There were no RPE changes at baseline prior to treatment, at all study points and in all study groups there did not appear to be any signs of significant posterior segment changes induced by the test articles. It is important to note that ERG scans performed on the nine animals prior to the intravitreal injections, as well as ERG scans performed on all the animals 1 day and 7 days post injection did not appear to cause any signs of significant change or toxicity induced by the test articles.

The second Intravitreal administration of 100 µl of 2.5% RGCysteic Acid solution to the group of six Rabbits numbers 902, 903, 905, 906, 907, 908, was not associated with any significant toxicity at all time points. There was no significant difference in reported adverse effects between the 2.5% RGCysteic Acid group and the isotonic saline solution group. This lack of toxicity was determined by clinical examination, indirect ophthalmoscopy and ultrasound β-scan and mechanical vitrectomy.

Slit lamp biomicroscopy was performed at all study visits and focused on the lids, conjunctiva and sclera, cornea, endothelial changes, anterior chamber reaction, iris, lens and capsule, as well as the anterior vitreous for signs for inflammation demonstrate a near complete lack of inflammatory reaction to intravitreal injections of 100 µl of 2.5% RGCysteic Acid solution and the isotonic saline solution group. At all study points and in all study groups there did not appear to be any signs of significant toxicity induced by the test articles.

Clinical evaluation of the posterior segment was also followed throughout the study to ensure that there was no significant retinal toxicity present. Indirect ophthalmoscopy as well as slit lamp fundus evaluations were carried out at each evaluation time point with specific attention to any signs of retinal toxicity. The posterior segment was evaluated for any changes in vitreous density, vitreous liquefaction, vitreous attachment, and possible hemorrhage. The retina was evaluated for any signs of RPE toxicity, retinal vascular compromise retinal hemorrhage, exudates, retinal tears, breaks, or detachments. There were no RPE changes at baseline 7 days prior to the second treatment, at all study points and in all study groups there did not appear to be any signs of significant posterior segment changes induced by the test articles. It is important to note that ERG scans performed on the six animals for a second time post the intravitreal injections, as well as ERG scans performed on all the animals 8 days and 14 days post injection did not appear to cause any signs of significant change or toxicity induced by the test articles.

The third Intravitreal administration of 100 μl of 2.5% RGCysteic Acid solution to the group of six Rabbits numbers 905, 906, 908, was not associated with any significant toxicity at all time points. There was no significant difference in reported adverse effects between the 2.5% RGCysteic Acid group and the isotonic saline solution group. This lack of toxicity was determined by clinical examination, indirect ophthalmoscopy and ultrasound β-scan and mechanical vitrectomy.

Slit lamp biomicroscopy was performed at all study visits and focused on the lids, conjunctiva and sclera, cornea, endothelial changes, anterior chamber reaction, iris, lens and capsule, as well as the anterior vitreous for signs for inflammation demonstrate a near complete lack of inflammatory reaction to intravitreal injections of 100 μl of 2.5% RGCysteic Acid solution and the isotonic saline solution group. At all study points and in all study groups there did not appear to be any signs of significant toxicity induced by the test articles.

Clinical evaluation of the posterior segment was also followed throughout the study to ensure that there was no significant retinal toxicity present. Indirect ophthalmoscopy as well as slit lamp fundus evaluations were carried out at each evaluation time point with specific attention to any signs of retinal toxicity. The posterior segment was evaluated for any changes in vitreous density, vitreous liquefaction, vitreous attachment, and possible hemorrhage. The retina was evaluated for any signs of RPE toxicity, retinal vascular compromise retinal hemorrhage, exudates, retinal tears, breaks, or detachments. There were no RPE changes at baseline 14 days prior to the third treatment, at all study points and in all study groups there did not appear to be any signs of significant posterior segment changes induced by the test articles. It is important to note that ERG scans performed on the three animals for a third time post the intravitreal injections, as well as ERG scans performed on all the animal 15 days and 21 days post injection did not appear to cause any signs of significant change or toxicity induced by the test articles.

Anti-Adhesive Properties of RGCysteic Acid Peptides: Kinetic Study of Wound Healing with Compound 1 (GRG Cysteic Acid TP), Cyclic-RGD and RGE In this example, in a model of wound healing, it has been demonstrated that RGCysteic Acid peptides have anti-adhesive properties and therefore can prevent development of many pathological vitreoretinal diseases and can inhibit metastases in human melanoma and colon cancer cells.

To test the anti-adhesive properties of RGCysteic Acid peptides in vitro, a wound-healing assay was performed with human umbilical vein endothelial cells (HUVEC). HUVEC were seeded and allowed to grow to a confluent monolayer on a fibronectin coated surface. A wound (a scratch rift) was created by dragging a small pipette tip across the HUVEC monolayer. The cells were then incubated in fresh growth medium containing the RGCysteic Acid peptide (Compound 1; 10 mM), and the wound area was imaged in five different fields at various time points (0, 4, 8, 12, 16, 20, 24 hours) to determine the kinetics of wound closure. The level of wound closure was quantified by determining the fraction of the original wound area that was re-occupied by HUVEC through cellular adhesion, migration and proliferation.

In control studies, the following peptides were used in place of RGCysteic Acid (Compound 1): cyclic-RGD peptide (1 mM), positive control) and RGE peptide (1 mM, negative control).

The effect of the peptides on the kinetics of wound healing is presented in FIG. 1. The results are shown as a percentage of the original area. The error bars correspond to the standard deviation in wound size across 2-6 independent trials. The results show that the RGCysteic Acid peptide inhibits HUVEC wound healing by 70% after 24 hours, while Cyclic RGD (RGD-based peptide; N-methylated cyclic-RGDf-N(Me)V; Cilengitide) inhibits HUVEC wound healing by 45% after 24 hours. These were both compared to a negative control RGE peptide that inhibited HUVEC wound healing by 0% after 24 hours. The effect of RGCysteic Acid (Compound 1) is quantitatively comparable to the activity of the RGD-based peptide, a well established inhibitor of integrin binding activity. Further, RGCysteic Acid peptide exhibits similar properties to the activities of the RGD-based peptide without apoptosis of the HUVEC cells. Both Cyclic RGD and Compound 1 are potent integrin inhibitors in this assay.

Cell interaction with the ECM through focal adhesion is a crucial element of cell migration that dictates the rate of wound closure. In two-dimensional cell migration, the anterior end of the cell with growing lamellipodia forms new adhesions with the substrate while the adhesions on the posterior end detach after cytoskeletal contraction, As described elsewhere herein, the strong adhesion between the vitreous and the retina could account for eventual development of many pathological vitreoretinal diseases such as vitreomacular traction, proliferative diabetic retinopathy, macular hole, age related macular degeneration and floaters. Thus, an atraumatic non-invasive approach to achieve a Posterior Vitreous Detachment, other than the mechanical separation of the vitreous from the inner retinal surface, is highly desirable (see Tezel, T. H. et al, Retina (1998) 18: 7-15; and Verstraeten, T. C, et al., Arch. Ophthalmol. (1993)111: 849-854).

As described elsewhere herein, it is believed that the ECM components, particularly collagen fibrils of the cortical vitreous, are anchored to the inner surface of the retina through integrin binding sites (see Foos, R. Y., Invest. Ophthalmol. Vis. Sci. (1972) 11:801-808) in the inner limiting lamella (ILL). It is also known that major adhesive glycoproteins of the ILL in the eye such as fibronectin and laminin, are heavily linked to integrins (see Curtis, T. M. et al., Am. J. Physiol., (1995) 269: L248-L260; Elner, S. G., et al., *IOVS* (1996) 37:696-701; and Horman, S. M, et al., Am. J. Physiol. (1995) 269: L248-L260) through the RGD (Arg-Gly-Asp) sequences and several integrins bind through RGD motif present in ECM proteins. Further, it is known that fibronectin binds to several other integrins besides $\alpha_v\beta_3$, whereas vitronectin is $\alpha_v\beta_3$-specific.

The primary connection of the integrins to the ECM involves the Arg-Gly-Asp(RGD)sequence and the RGD sequence binds to a shallow crevice located between the α- and β-subunits of the integrin head (see Xiong, et al., Science (2002) 296: 151-155). Such binding helps modulate various cellular signaling pathways, including cell adhesion, migration, differentiation, angiogenesis and wound healing (see Ruoslahti, E., et al., Science (1987) 238: 491-497; and J. Clin. Invest. (1991) 87: 1-5).

Since the vitreous extracellular matrix; e.g., collagen fibrils are connected to the cellular retina by the integrin binding sites, intravitreal injection of RGCysteic Acid peptides (oligopeptides) could release the RGD motif of the vitreous extracellular matrix from the cellular retina by a competitive binding to the same integrin receptor sites.

Several investigators (see Ruoslahti, E. et al., Science (1987) 238: 491-497; Hynes, R. A., et al., Cell (1992) 68: 303-322; and Humphries, M. J., J. Cell Sci., (1990) 97: 585-592) demonstrated that many integrins ($\alpha_v\beta_3$, $\alpha_5\beta_1$, $\alpha_{11}\beta_3$, etc.) can be inhibited by small peptides that possess the RGD sequence motif. It is also well documented that that $\alpha_v\beta_3$ and $\alpha_5\beta_1$ integrins, as well as vitronectin and fibronectin, were upregulated in tumors such as human melanoma cells (see Nip, J., J. Clin. Invest., (1992) 90: 1406-1413), human breast cancer cells (see Rong, L. et al., Invest. Ophthalmol. Vis. Sci. (2009) 50: 5988-5996), and human retinal pigment epithelial cells (Peter C. Brooks, et al., J. Clin. Invest., (1995) 96: 1815-1822). Thus it has been demonstrated that there is good correlation between metastatic potentials of human melanoma cells and adhesion of melanoma cells to lymph node vitronectin via the $\alpha_v\beta_3$ integrin receptor and that the adhesion was inhibited by an RGD containing peptide (Nip, J., J. Clin. Invest., (1992) 90: 1406-1413). This demonstrates that RGDpeptides can be an important anti-angiogenic agents.

Further, it has been demonstrated in a human colon cancer cell line that when there is significant increase in cell adhesion, then there is increased metastatic activity (Lehmann, M., Cancer Res., (1994), 54: 2102-2107). Therefore agents that inhibit cell adhesion effectively inhibit colon cancer and melanoma from metastasizing.

Based on the results of the wound healing study where RGCysteic Acid has been shown to inhibit cell adhesion, and upon extrapolation of the metastatic potential of RGD in the Melanoma and Colon cancer models, RGCysteic Acid peptides and their derivatives can effectively inhibit tumor metastases, for example, in melanoma and colon cancer.

Use of RGCysteic Acid Peptides for Directing or Delivering Agents to Tumors

In this example, a dimeric RGCysteic Acid Peptide-Paclitaxel conjugate (Compound 3), shown below, is provided. This composition is useful as an antitumor agent. The dimeric RGCysteic Acid Peptide selectively binds to integrin receptors that are highly expressed in certain cancer cells and is useful to treat certain metastatic cancers such as, for example, metastatic breast cancer, by inhibiting cell adhesion.

Compound 3:

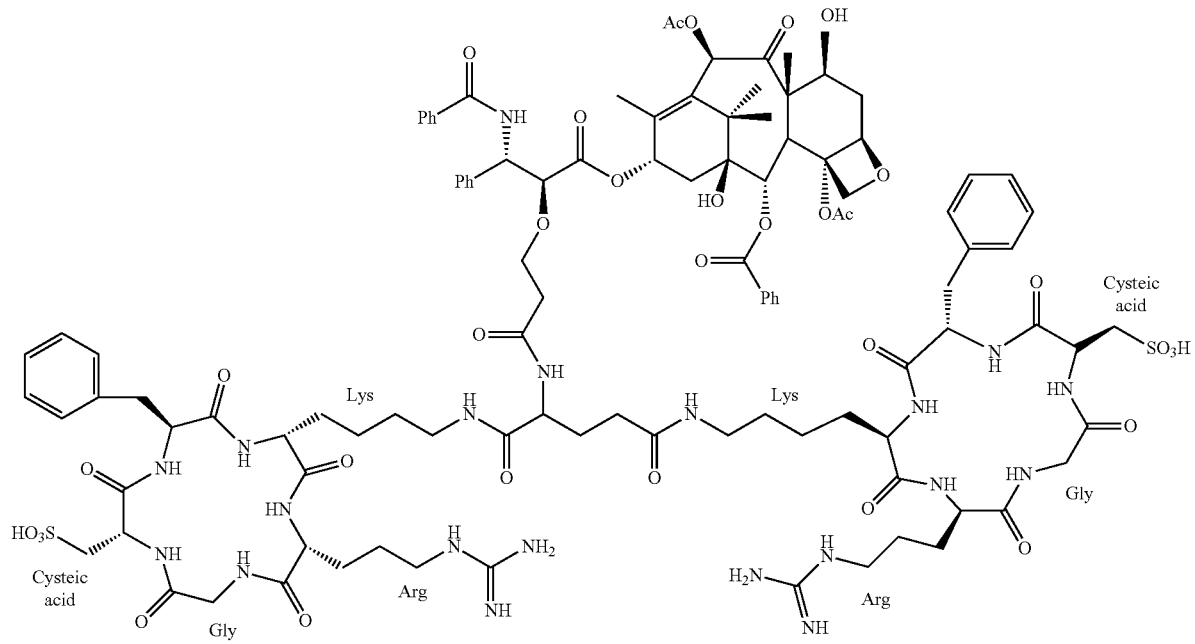

Compound 3

The synthesis and mechanisms of action, biodistribution and tumor selectivity of the corresponding RGD analogue of Compound 3 are as described in Chen, X., et al.; Synthesis and Biological Evaluation of Dimeric RGD Peptide-Paclitaxel Conjugate as a Model for Integrin-Targeted Drug Delivery; J. Med. Chem., (2005) 48 (4): 1098-1106).

Although Compound 3 comprises a particular anti-tumor agent, Paclitaxel, bound to dimeric RGCysteic Acid peptide, it is to be appreciated that this aspect of the invention includes all monomeric or multimeric forms of RGCysteic Acid peptides bound to any feasible diagnostic or therapeutic agents that may be useful in diagnosing, imaging or treating a tumor or other integrin-containing tissue or structure. Examples of antitumor substances that may be bound to monomeric or multimeric RGCysteic Acid peptides in accordance with this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular. DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), anti-tumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, triazole inhibitors such as letrozole and anastrazole, steroidal inhibitors such as exemestane), anti-angiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, chlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

$^{64}$CU-Labeled Multimeric RGCysteic Acid Peptides for Imaging Integrin-Expressive Tumors In this example, $^{64}$CU-Labeled tetrameric and octameric RGCysteic Acid peptides of the present invention (Compounds 4 and 5 respectively), shown below, are useful as radiotherapeutic agents for imaging and diagnostic purposes (e.g., radiolabeling of tumors for PET scanning) as well as for directing or delivering therapeutic agents to tumors or other cells which express integrins, such as tumors which express $\alpha_v\beta_3$ integrins.

Compound 4:

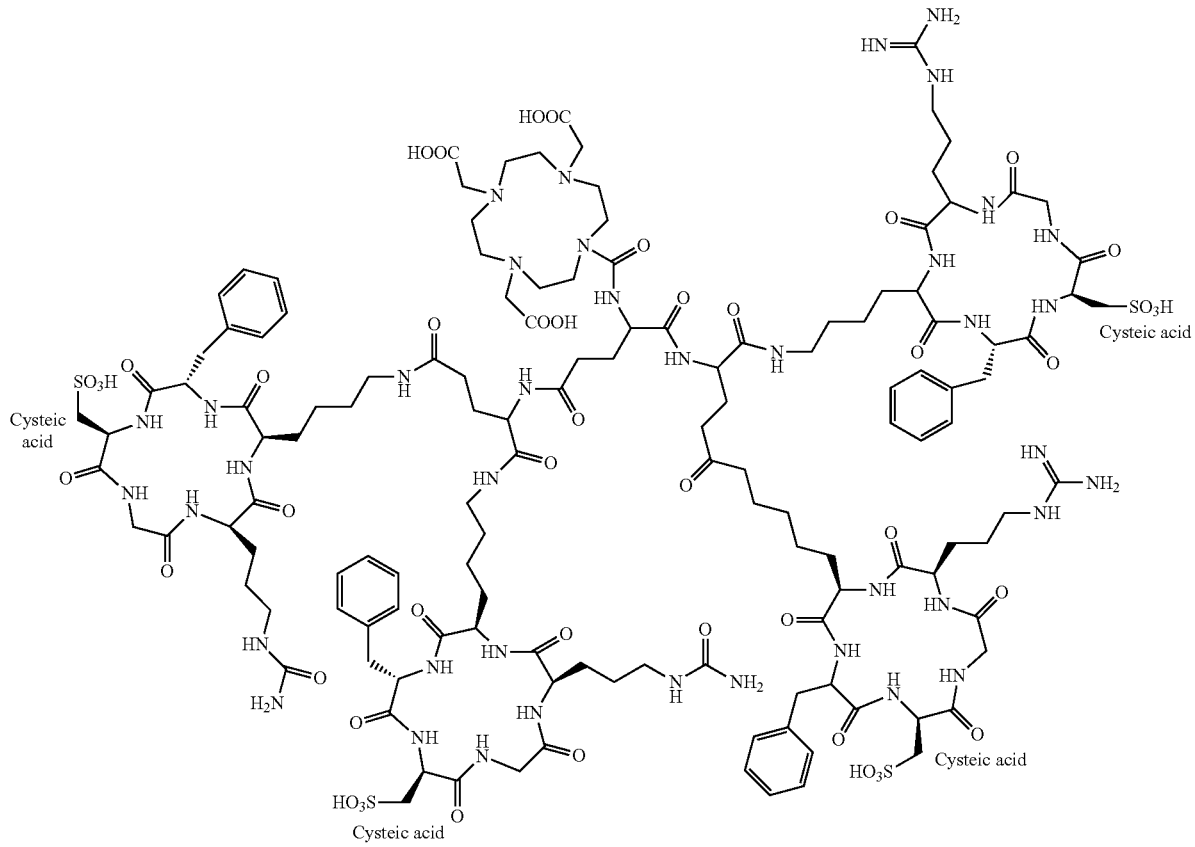

COMPOUND 4

Compound 5:

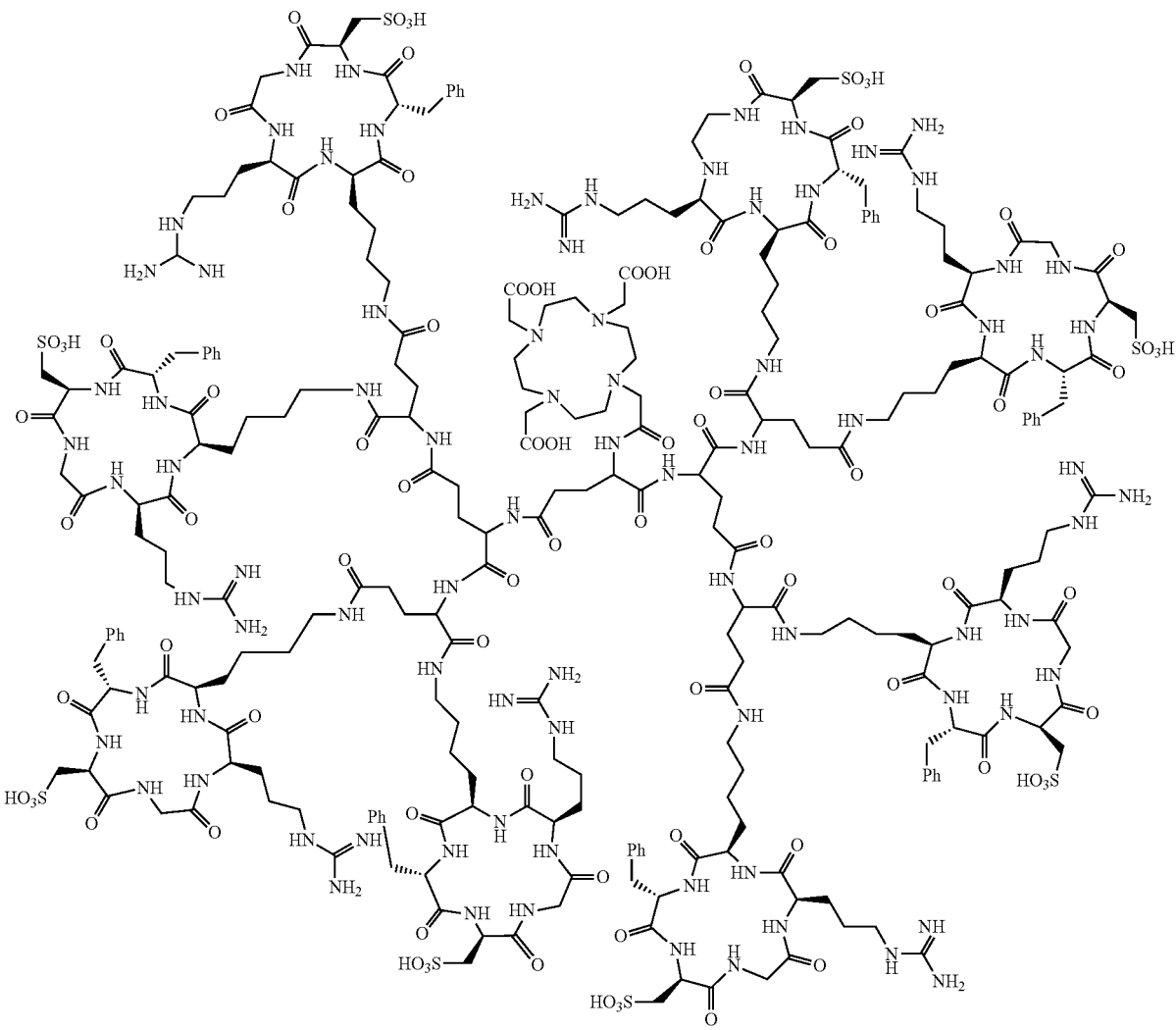

Compound 5

The synthesis and mechanisms of action, biodistribution, tumor selectivity and PET related use of the corresponding RGD analogues of Compounds 4 and 5 are as described in Li, Z. et al., [64]CU-Labeled Tetrameric and Octameric RGD Peptides for Small-Animal PET of Tumor $\alpha_v\beta_3$ Integrin Expression; J. Nucl. Med. 48 (7) pp. 1162-1171 (2007).

Suppression Of Choroidal Neovascularization (CNV) In Vivo By Compound 1

In this example, Compound 1 was tested to determine whether it CNV in a published mouse model. See, Umeda N, Kachi S, Akiyama H, Zahn G, Vossmeyer D, Stragies R, Campochiaro P., Suppression and Regression of Choroidal Neovascularization by Systemic Administration of an $\alpha_5\beta_1$ Integrin Antagonist: *Molecular Pharmacology:* 2006, 69, 1820-1828.

Figure 8:
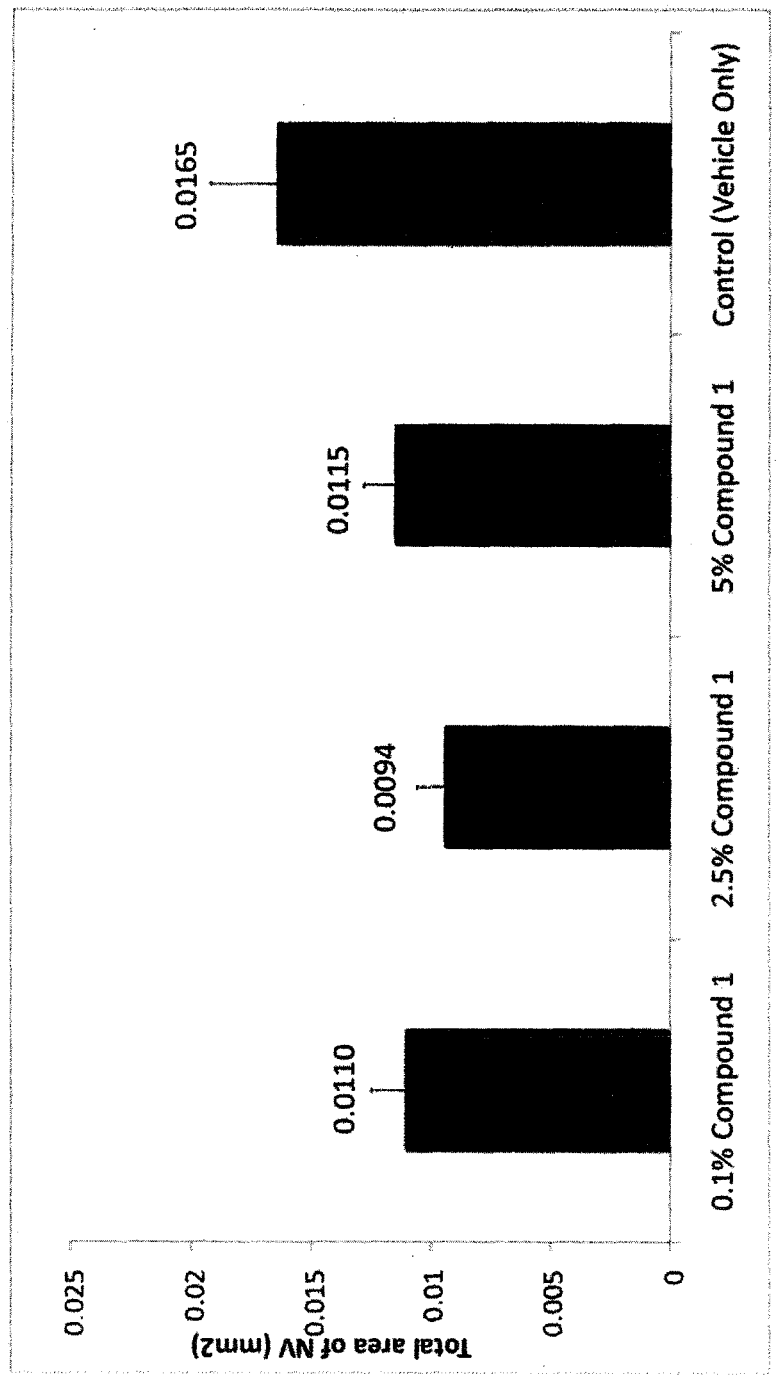
FIG. 8 is a graph showing total area of neovascularization in a CNV mouse model 14 days after treatment with various doses of Compound 1 and control (vehicle only).

The study mice had laser-induced rupture of Bruch's membrane followed by an intravitreal injection of a single dose of COMPOUND 1 at the concentration of 1.0 µg/1 µL, 25 µg/1 µL and at 50 µg/1 µL, as well as a vehicle immediately after laser treatment. Fourteen days after laser treatment, the area of CNV was measured by image analysis. The size of CNV lesions appeared somewhat smaller in the eyes treated with 1.0 µg/1 µL and the 50 µg/1 µL concentrations of COMPOUND 1. FIG. 8 is a graph showing total area of neovascularization in a CNV mouse model 14 days after treatment with various doses of Compound 1 and control (vehicle only).

The 25 µg/1 µL concentration of Compound 1 exhibited a statistically significant 43% reduction in CNV compared to vehicle treated eyes. This suggests that a single intravitreal injection of Compound 1 at 25 µg/1 µL is sufficient to significantly inhibit CNV.

In-Vivo Study—Rop Model for Diabetic Retinopathy

In this Example, Compound 1 was tested in an ischemic retinopathy mouse model to explore the feasibility of suppressing pre-retinal neovascularization.

Figure 9:
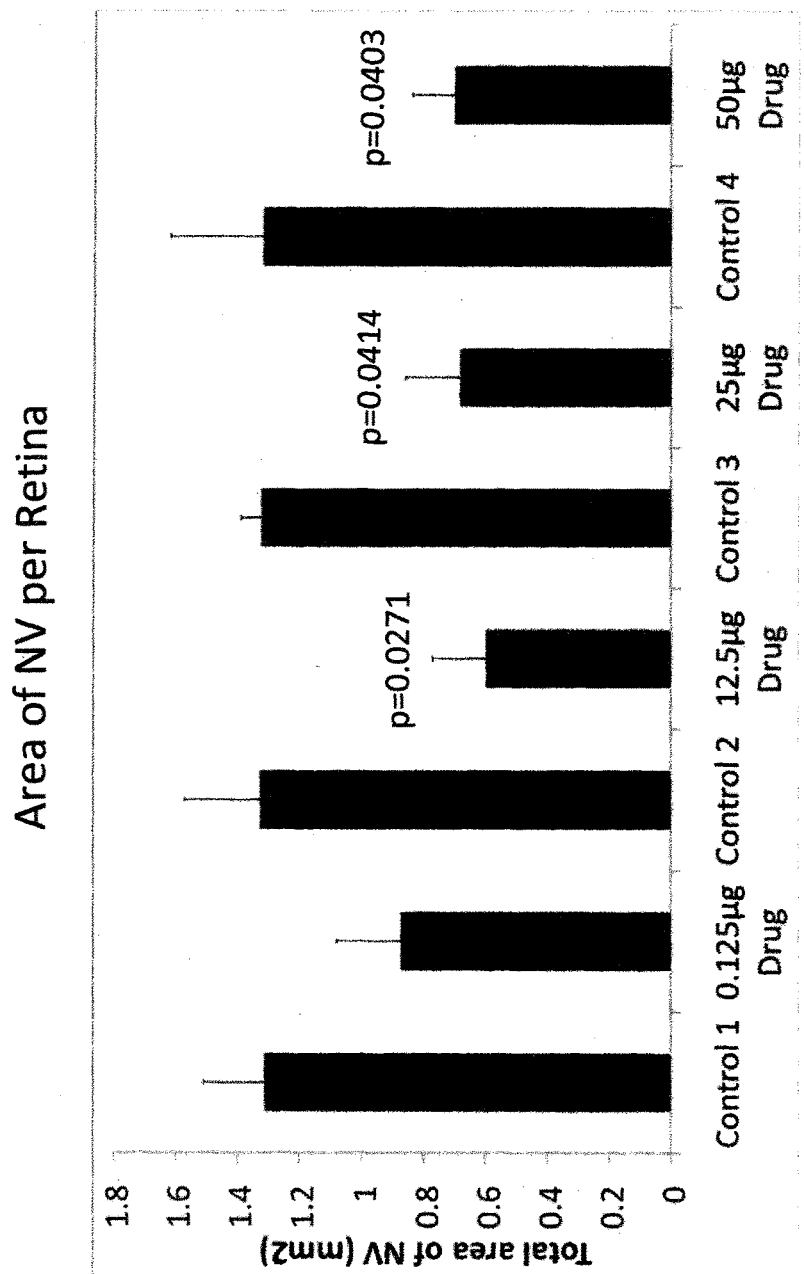
FIG. 9 is a bar graph comparing the measured area of neovascularization in an ROP mouse model following various doses of compound 1 and control (vehicle only).
Figure 10D:
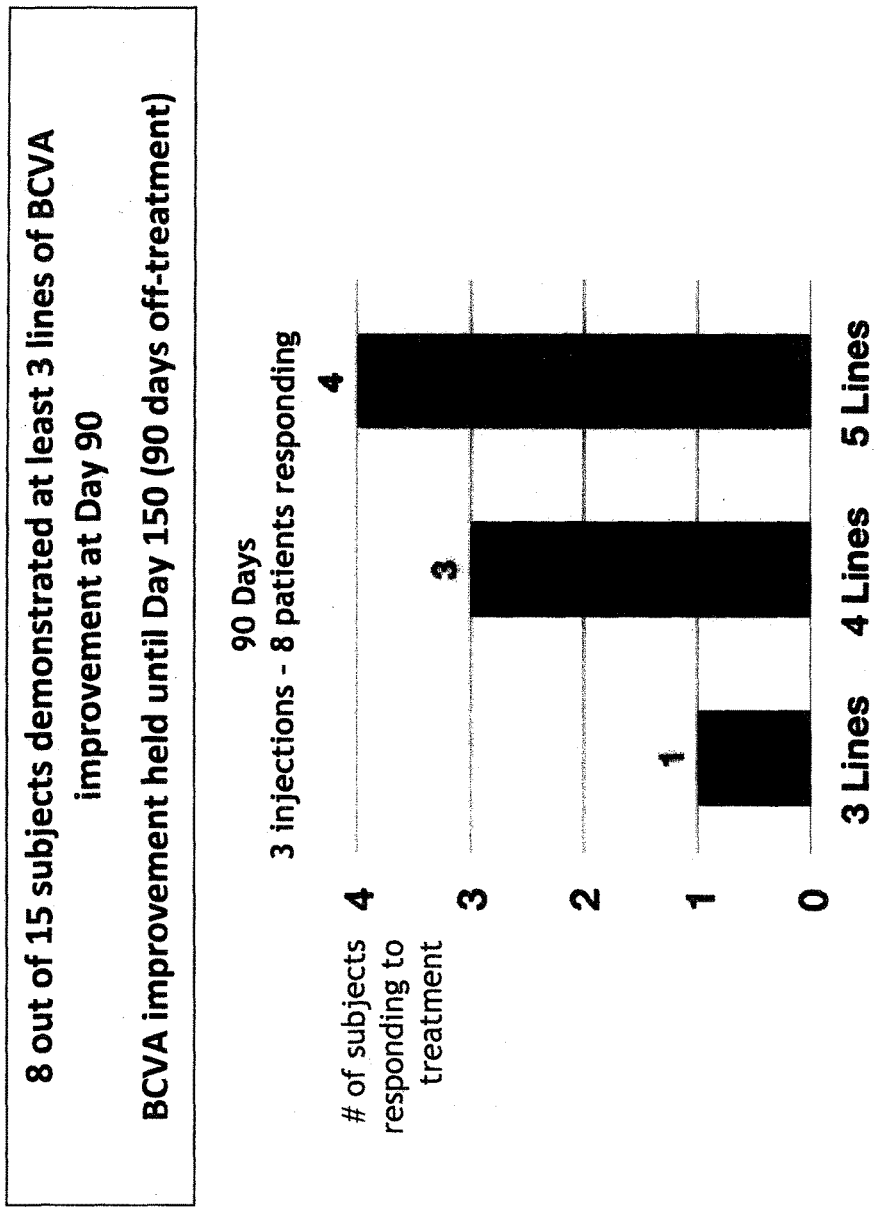
Figure 10E:
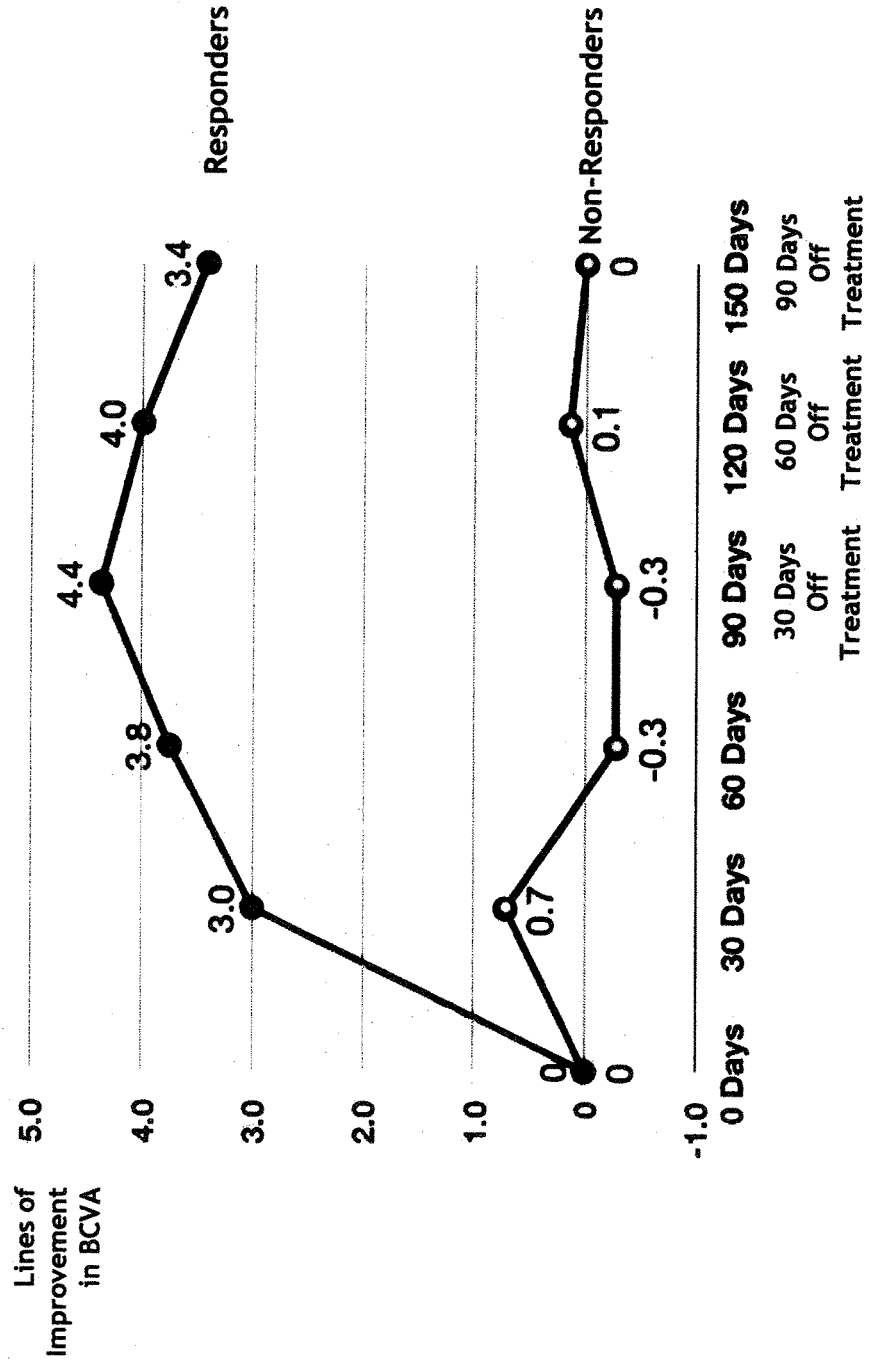
Figure 10F:
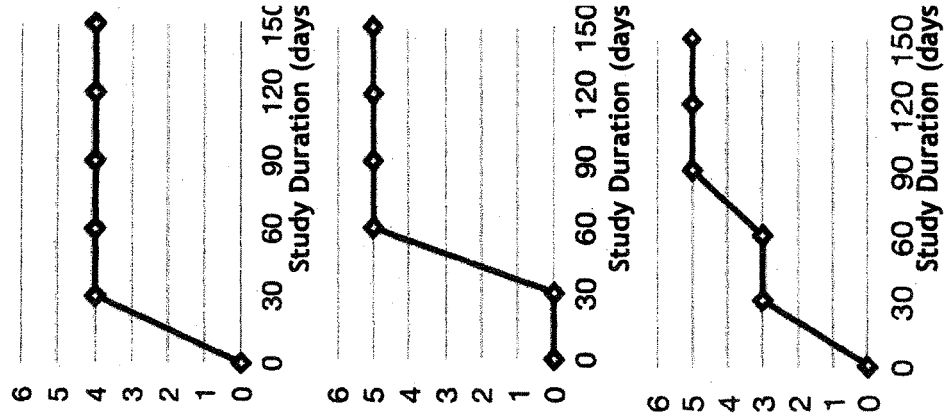
Figure 10G:
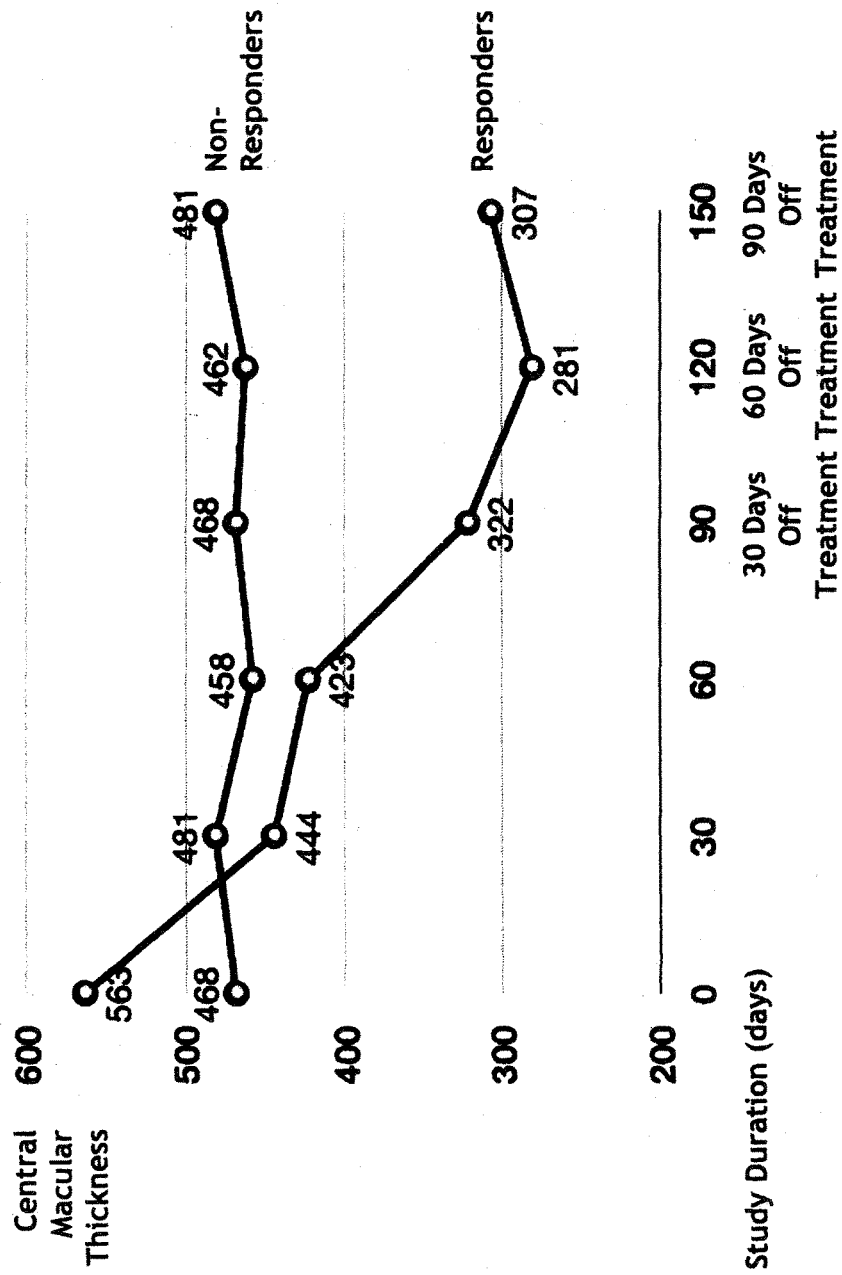
Figure 10H:
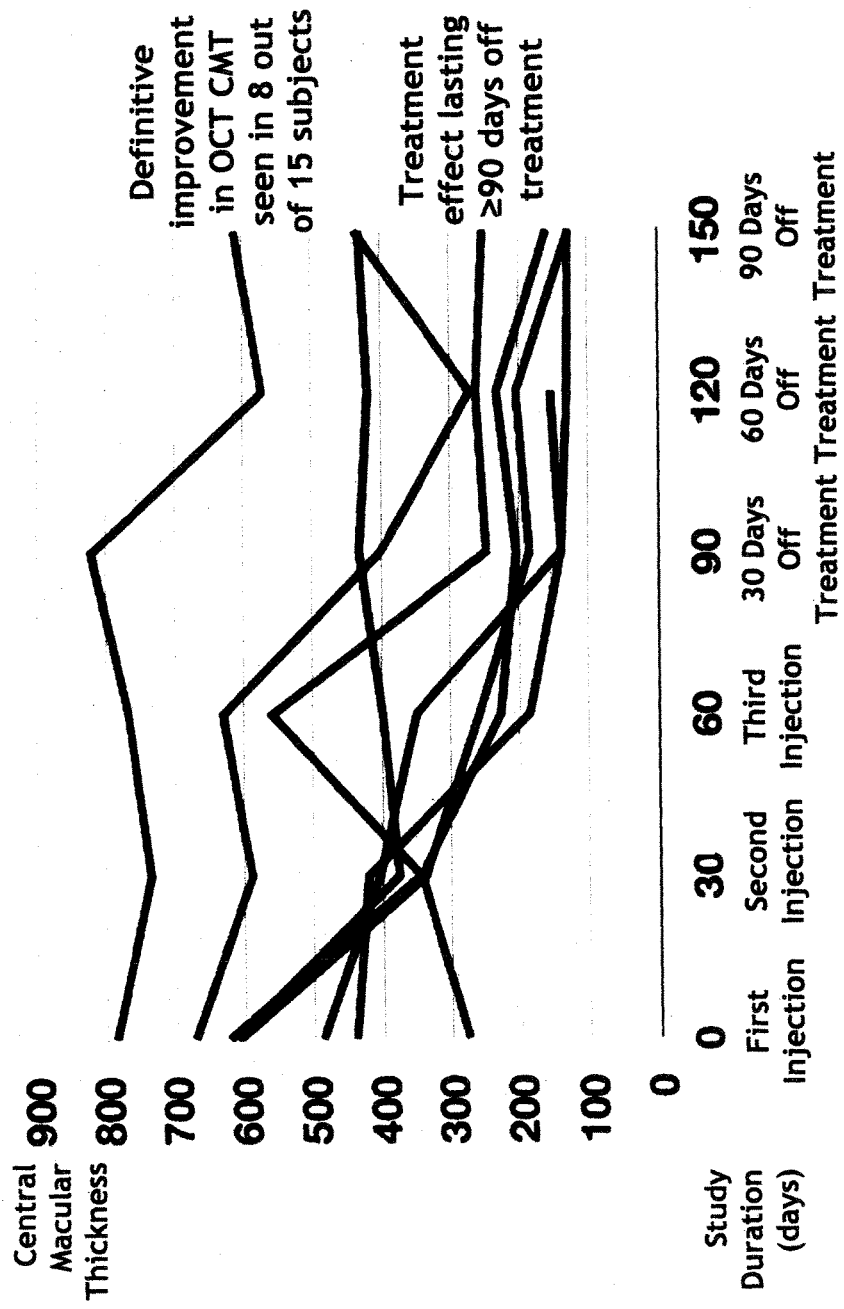
Figure 10I:
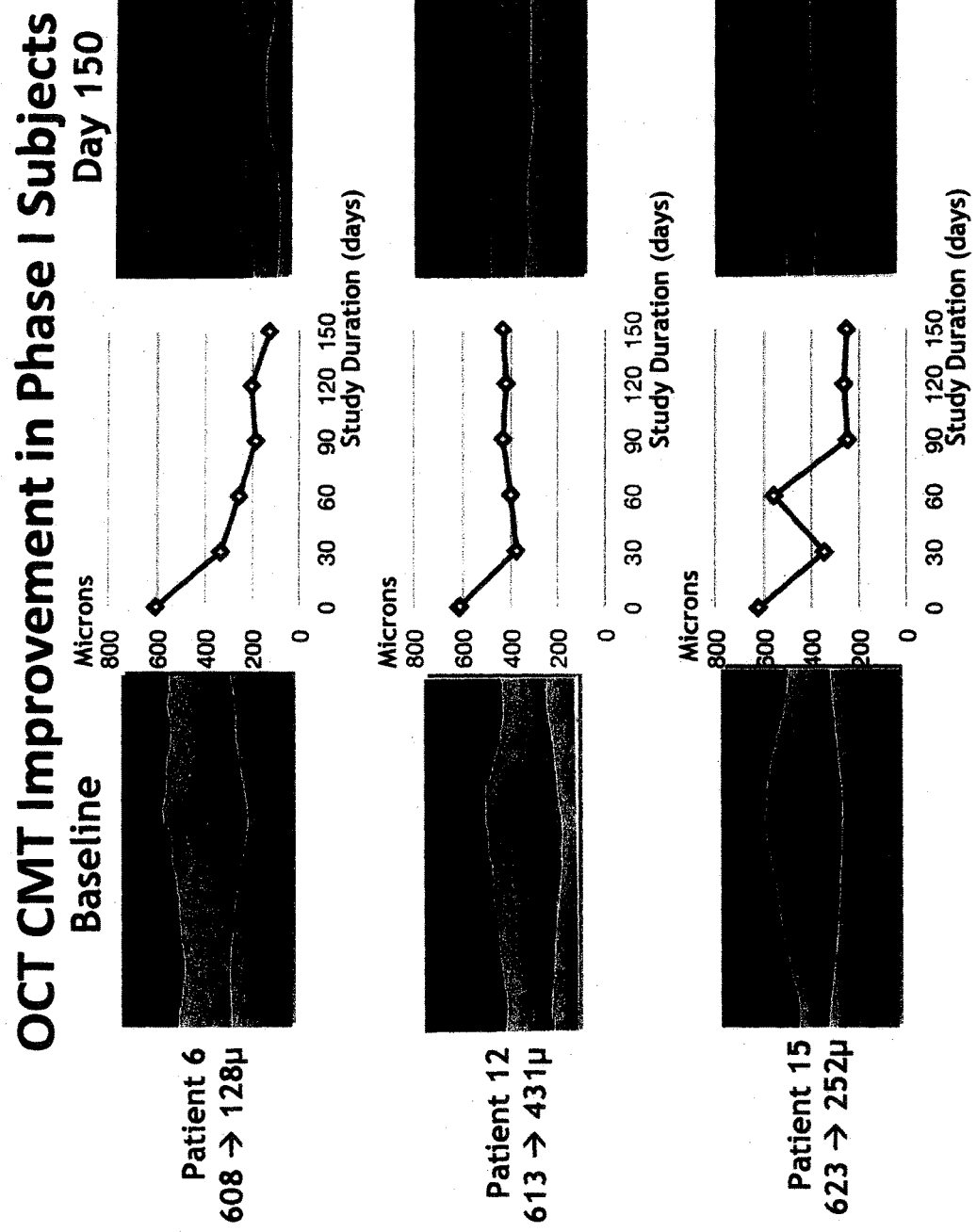
Figure 10J:
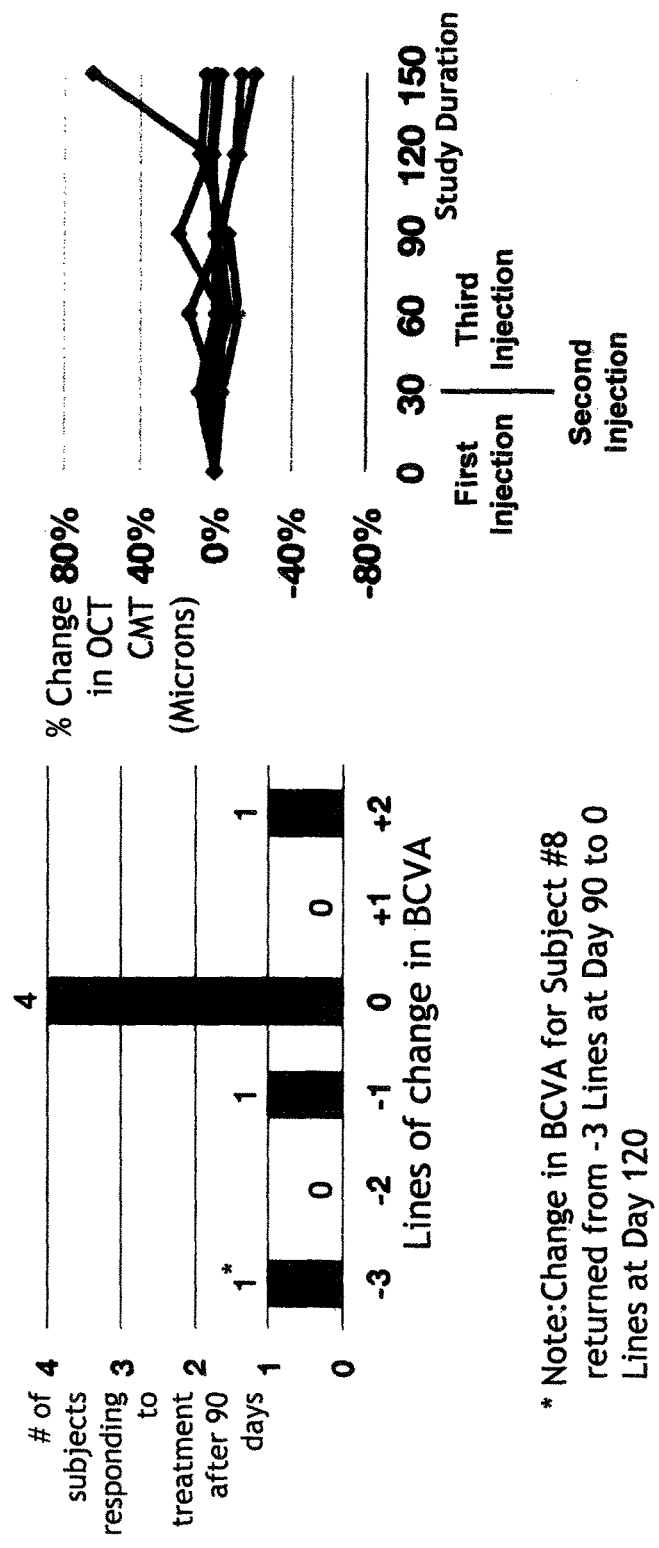

Mice that had ischemic retinopathy were injected intravitreously with a single dose of Compound 1 at the concentration of 0.125 μg/1 μL, 12.5 μg/1 μL, 25.0 μg/1 μL and at 50.0 μg/1 μL (Groups B, D, F and H, respectively), as well as a vehicle (BSS) (Controls 1, 2, 3 and 4) on post-natal day 12. On post-natal day 17, 5 days after intravitreal injection, the area of neovascularization was measured by image analysis. FIG. 9 is a bar graph comparing the measured area of neovascularization in mice treated with these varying doses of compound 1 or control (vehicle only). As shown in FIG. 9, the size of neovascularization lesions appeared somewhat smaller in the eyes treated with (B) 0.125 μg/1 μL. However, Groups D (12.5 μg/1 μL), F (25.0 μg/1 μL) and H (50.0 μg/1 μL) were all greatly decreased and all three concentrations were found to be statistically significant compared to Controls 2, 3 and 4.

The results of this study suggest that a single intravitreal injection of Compound 1 at 12.5 μg/1 μL, 25.0 μg/1 μL and at 50.0 μg/1 μL is sufficient to significantly inhibit pre-retinal neovascularization.

Animal Toxicology of Compound

The following Tables A through E summarize animal toxicity data obtained from the following studies:

| Study Title |
| --- |
| Ocular Toxicity of Intravitreal Injection of 2.5 mg/100 μl of COMPOUND 1 With and Without Urea in New Zealand Rabbits |
| Ocular Toxicity of Intravitreal Injection of 2.5 mg/100 μl of COMPOUND 1 and 2.5 mg/100 μl of RGD In New Zealand Rabbits |
| Ocular Toxicity of Subconjunctival Injection of 5.0 mg/100 μl of COMPOUND 1 in New Zealand Rabbits |
| Ocular Toxicity of Three Intravitreal Injections of 2.5 mg/100 μl of COMPOUND 1 Containing 0.02% Disodium EDTA in New Zealand Rabbits |
| Ocular Toxicity Dose Escalation Study of Multiple Injections of COMPOUND 1 at 2.5 mg/100 μL, 5.0 mg/100 μL, and 10.0 mg/100 μL in Pigmented New Zealand Rabbits |

TABLE A

OCULAR TOXICITY OF INTRAVITREAL INJECTION OF 2.5 MG/100 μL OF COMPOUND 1 WITH AND WITHOUT UREA IN NEW ZEALAND RABBITS

| STUDY OBJECTIVE | STUDY GROUPS | STUDY PARAMETERS | RESULTS |
| --- | --- | --- | --- |
| Ocular toxicity after single intravitreal injection of 2.5 mg/100 μL of COMPOUND 1 with and without Urea, as well as control | Group 1: 8 eyes injected with 2.5 mg/100 μL of COMPOUND 1 Group 2: 8 eyes injected with 2.5 mg/100 μL of COMPOUND 1 and 12% Urea solution. Group 3: 8 eyes injected with 12% Urea solution. Group 4 (Control): 4 eyes injected with BSS | 24 hour follow up after single injection Ocular toxicity: Ocular adverse events Slit lamp biomicroscopy Indirect ophthalmoscopy β-Scan Mechanical vitrectomy Pharmacologic effect: Vitreous liquefaction Induction of PVD | Ocular toxicity: No inflammation No cataract formation No RPE toxicity No retinal vascular compromise No retinal hemorrhage No exudates No retinal tears, breaks or detachments Pharmacologic effect: Group 1: 75% Total PVD Complete liquefaction Group 2: 88% Total PVD Complete liquefaction Group 3: 0% Total PVD No liquefaction Group 4: 0% Total PVD No liquefaction |

TABLE B

OCULAR TOXICITY OF INTRAVITREAL INJECTION OF 2.5 MG/100 μL OF COMPOUND 1 AND 2.5 MG/100 μL OF RGD IN MALE AND FEMALE NEW ZEALAND RABBITS

| STUDY OBJECTIVE | STUDY GROUPS | STUDY PARAMETERS | RESULTS |
| --- | --- | --- | --- |
| Ocular toxicity after single intravitreal injection of 2.5 mg/100 μL of | Group 1: 5 eyes injected with 2.5 mg/100 μL of COMPOUND 1 | 24 hour follow up after single injection Ocular toxicity: Ocular adverse | Ocular toxicity: No inflammation No cataract formation No RPE toxicity |

TABLE B-continued

OCULAR TOXICITY OF INTRAVITREAL INJECTION OF 2.5 MG/100 µL OF
COMPOUND 1 AND 2.5 MG/100 µL OF RGD IN MALE AND FEMALE NEW ZEALAND
RABBITS

| STUDY OBJECTIVE | STUDY GROUPS | STUDY PARAMETERS | RESULTS |
|---|---|---|---|
| COMPOUND 1 with and without EDTA, and 2.5 mg/100 µL of RGD with and without EDTA, as well as untreated controls and BSS control | Group 2: 5 eyes injected with 2.5 mg/100 µL of COMPOUND 1 + 0.02% EDTA<br>Group 3: 5 eyes injected with 2.5 mg/100 µL of RGD<br>Group 4: 5 eyes injected with 2.5 mg/100 µL of RGD + 0.02% EDTA<br>Group 5: (Control): 10 eyes injected with BSS<br>Group 6: (Control): 10 eyes untreated controls | events<br>Slit lamp biomicroscopy<br>Indirect ophthalmoscopy<br>β-Scan<br>Mechanical vitrectomy<br>Pharmacologic effect:<br>Vitreous liquefaction<br>Induction of PVD | No retinal vascular compromise<br>No retinal hemorrhage<br>No exudates<br>No retinal tears, breaks or detachments<br>Pharmacologic effect:<br>Group 1:  60% Total PVD<br>         80% Complete Liquefaction<br>Group 2:  50% Total PVD<br>         50% Complete Liquefaction<br>Group 3:  60% Total PVD<br>         80% Complete liquefaction<br>Group 4:  40% Total PVD<br>         40% Complete liquefaction<br>Group 5:  11% Total PVD<br>         22% Complete liquefaction<br>Group 6:  0% Total PVD<br>         20% Complete liquefaction |

TABLE C

OCULAR TOXICITY OF SUB-CONJUNCTIVAL INJECTION OF
5.0 MG/100 µL OF COMPOUND 1 IN NEW ZEALAND RABBITS

| STUDY OBJECTIVE | STUDY GROUPS | STUDY PARAMETERS | RESULTS |
|---|---|---|---|
| Ocular toxicity after single subconjunctival injection of 5.0 mg/100 µL of COMPOUND 1, as well as control | Group 1: 3 eyes injected with 5.0 mg/100 µL of COMPOUND 1<br>Group 2: 3 eyes injected with isotonic saline solution | 48 hour follow up after single injection<br>Ocular toxicity<br>Ocular adverse events<br>Slit lamp biomicroscopy<br>Indirect ophthalmoscopy<br>β-Scan<br>Mechanical vitrectomy<br>Pharmacologic effect:<br>Vitreous liquefaction<br>Induction of PVD | Ocular toxicity:<br>No inflammation<br>No cataract formation<br>No RPE toxicity<br>No retinal vascular compromise<br>No retinal hemorrhage<br>No exudates<br>No retinal tears, breaks or detachments<br>Pharmacologic effect:<br>Group 1:<br>0% Total PVD<br>No liquefaction<br>Group 2:<br>0% Total PVD<br>No liquefaction |

TABLE D

OCULAR TOXICITY OF THREE INTRAVITREAL INJECTION OF
2.5 MG/100 µL OF COMPOUND 1 NEW ZEALAND RABBITS

| STUDY OBJECTIVE | STUDY GROUPS | STUDY PARAMETERS | RESULTS |
|---|---|---|---|
| Ocular toxicity after three intravitreal injections of | Group 1: 3 eyes injected 1X with 2.5 mg/100 µL of COMPOUND 1 + 0.02% EDTA solution | Three groups injected up to 3x with 2.5 mg/100 µL of COMPOUND 1 + 0.02% EDTA solution, with | Ocular toxicity:<br>No inflammation<br>Small number of cataracts |

TABLE D-continued

OCULAR TOXICITY OF THREE INTRAVITREAL INJECTION OF 2.5 MG/100 µL OF COMPOUND 1 NEW ZEALAND RABBITS

| STUDY OBJECTIVE | STUDY GROUPS | STUDY PARAMETERS | RESULTS |
|---|---|---|---|
| 2.5 mg/100 µL of COMPOUND 1, as well as control | Group 2: 3 eyes injected 1X with sterile isotonic saline solution<br>Group 3: 3 eyes injected 2X with 2.5 mg/100 µL of COMPOUND 1 + 0.02% EDTA solution<br>Group 4: 3 eyes injected 2X with sterile isotonic saline solution<br>Group 5: 3 eyes injected 3X with 2.5 mg/100 µL of COMPOUND 1 + 0.02% EDTA solution<br>Group 6: 3 eyes injected 3X with sterile isotonic saline solution | assessments at Days 7, 14 and 21<br>Ocular toxicity<br>Ocular adverse events<br>Slit lamp biomicroscopy<br>Indirect ophthalmoscopy<br>ERG<br>Histopathology<br>Electron Microscopy<br>Pharmacologic effect:<br>Ocular Toxicity | No RPE toxicity<br>No retinal vascular compromise<br>No retinal hemorrhage<br>No exudates<br>No retinal tears, breaks or detachments<br>Pharmacologic effect:<br>Groups 1, 3, 5:<br>No Ocular Toxicity<br>Groups 2, 4, 6:<br>No Ocular Toxicity |

TABLE E

OCULAR TOXICITY OF THREE INTRAVITREAL INJECTIONS OF 2.5 MG/100 µL, 5.0 MG/100 µL AND 10.0 MG/100 µL OF COMPOUND 1 IN PIGMENTED NEW ZEALAND RABBITS

| STUDY OBJECTIVE | STUDY GROUPS | STUDY PARAMETERS | RESULTS |
|---|---|---|---|
| Ocular toxicity after three intravitreal injections of 2.5 mg/100 µL, 5.0 mg/100 µL and 10.0 mg/100 µL of COMPOUND 1, as well as Balanced Salt Solution | Group 1: 2 rabbits, with 1 injected 2x and 1 injected 3x @ 2.5 mg/100 µL of COMPOUND 1<br>Group 2: 3 rabbits, with 1 injected 1x, 1 injected 2x and 1 injected 3x @ 5.0 mg/100 µL of COMPOUND 1<br>Group 3: 3 rabbits, with 1 injected 1x, one injected 2x and one injected 3x @ 10.0 mg/100 µL of COMPOUND 1<br>Control: Contralateral eye in each rabbit injected with Balanced Salt Solution at time of injection of treated eye | 1. Groups 2 and 3 each had 1 rabbit sacrificed on Day 7 after one injection of COMPOUND 1<br>2. Groups 1, 2 and 3 each had 1 rabbit sacrificed on Day 37 after two injections of ALG-1001<br>3. Groups 1, 2 and 3 each had 1 rabbit sacrificed on Day 90 after 3 injections of COMPOUND 1<br>Ocular toxicity<br>Ocular adverse events<br>Slit lamp biomicroscopy<br>Indirect ophthalmoscopy<br>Tonometry<br>ERG<br>Histopathology<br>Electron Microscopy | Ocular toxicity:<br>No inflammation<br>No cataract formation<br>No RPE toxicity<br>No retinal vascular compromise<br>No retinal hemorrhage<br>No exudates<br>No retinal tears, breaks or detachments<br>Pharmacologic effect:<br>Tonometry:<br>12.7 mmHg average for COMPOUND 1 treated eyes<br>13.2 mmHg average for BSS treated eyes<br>ERGs:<br>Normal ERGs for COMPOUND 1 treated eyes<br>Normal ERGs for BSS treated eyes<br>Histopathology:<br>Normal for COMPOUND 1 treated eyes<br>Normal for BSS treated eyes |

Human Multiple Dose Study

Fifteen human patients with late stage DME received three monthly intravitreal injections of Compound 1 as part of a multiple-injection Phase 1 Human Safety Study. There were no Serious Adverse Events and no Significant Adverse Events. While this study was firstly a safety study, efficacy was also assessed. Eight of the patients improved three or more lines in BCVA (representing 53% of the treated patients) and four of the patients improved from nearly legally blind to functional vision in the 20/40 to 20/60 range. Additionally, significant improvement in macular anatomy on OCT was observed in eight patients, ranging from 30% to 80%. These improvements in BCVA and OCT central macular thickness persisted for 90 days of follow up off treatment. These results have been achieved despite the fact that these human patients suffered from late stage DME and many had been deemed refractory to current treatment options of both Avastin as well as photocoagulation laser. The following Table F shows a summary of those study patients who had received prior treatment with Avastin or photocoagulation laser therapy:

TABLE F

| Subject # | Prior Treatment | # of Days Between Prior Treatment and First Compound 1 Injection | # of Days Between Prior Treatment and First Material Clinical Benefit | 90-Day/ 150-Day Change in BCVA (Lines) | 150-Day Change in OCT CMT (&) |
|---|---|---|---|---|---|
| 004 | Avastin | 90 | 150 | 0/0 | −21% |
| 006 | Avastin Laser | 90 | 120 | +4/+4 | −79% |
| 007 | Avastin | 120 | 180 | +3/+1 | +4% |
| 009 | Avastin Laser | 90 | 120 | +5/+5 | −14% |
| 017 | Laser | 270 | 360 | +4/+4 | −35% |

Further details and results of this study are shown the following Table F, in the graphs and diagrams of FIGS. 10A through 10I and the written paragraphs below.

TABLE G

SAFETY AND EFFICACY OF THREE INTRAVITREAL INJECTIONS OF 2.5 MG/100 µL OF COMPOUND 1 IN HUMAN SUBJECTS WITH DIABETIC MACULAR EDEMA
CLINICAL TRIAL SUMMARY

| STUDY OBJECTIVE | STUDY GROUP | STUDY PARAMETERS | RESULTS |
|---|---|---|---|
| 150-day study to test safety of 2.5 mg/100 µL of COMPOUND 1, intravetrially injected once per month for three months with three months of follow-up | 15 DME patients with BCVA of 20/100 or worse, many of whom are refractory to standard of care | Safety: Ocular adverse events BCVA-ETDRS Indirect ophthalmoscopy Slit lamp biomicroscopy Fundus photography Fluorescein angiography Ultrasonography OCT ERG examinations Efficacy: Improvement of BCVA-ETDRS Reduction of central macular thickness PVD induction | Safety: No SAEs or significant AEs throughout the study No reduction of BCVA-ETDRS No ERG changes Efficacy: 8 of 15 subjects improved BCVA by three to five lines 8 of 15 patients achieved a reduction in CMT by 30% to 80% 7 out of 15 subjects had no material change in BCVA 7 out of 15 patients had no material increase in CMT 55% of subjects had PVD induction |

The objective of the Phase 1 study was to evaluate the safety and initial efficacy of the ophthalmic intravitreal injection of COMPOUND 1 in human subjects with end stage diabetic macular edema (DME). The primary endpoint of this study was the observation of dose limiting toxicity. A secondary endpoint of this study was observation of a clinical benefit in reducing the diabetic macular edema in BCVA (ETDRS lines) and OCT central macular thickness.

Fifteen human subjects with chronic end-stage DME completed this open label study. Subjects at enrollment had BCVA of 20/100 or worse primarily due to DME and had not undergone anti-VEGF treatment or focal laser within 90 days prior to enrollment. Many study subjects were refractory to previous Avastin treatments. Study subjects received three monthly intravitreal injections of 2.5 mg COMPOUND 1 and were followed monthly for an additional 3 months. Safety measurements were followed by BCVA, slit lamp evaluation, dilated fundus exam, IOP measurements, OCT, FA, Fundus Photos, B-scan ultrasound, and ERG.

A total of 15 subjects were enrolled in this study. Overall, all study subjects tolerated the study drug COMPOUND 1 extremely well. There were no reports of inflammatory reactions either in the anterior chamber or vitreous cavity. No sustained elevations in IOP were noted. No corneal decompensation or cataract progression was noted during this study. No retinal tears or retinal detachments were noted during this study, however a high incidence (55%) of posterior vitreous detachment was observed by B-scan ultrasound as seen in previous rabbit studies. Furthermore, no vascular occlusions were observed throughout the course of these studies. Of the 15 subjects, there were no Serious Adverse Events or significant Adverse Events reported.

53% (8 out of 15) of the subjects reported a 3 line or more increase in BCVA by study day 90 after receiving 3 intravitreal injections. No study subject lost BCVA from baseline. Interestingly, the same proportion of subjects (53% or 8 out of 15) were noted to have a significant reduction in OCT central macular thickness of at least 30%. The maximum reduction in macular edema was 505 microns (608 to 103), a nearly 80% reduction in macular edema. Improvements in BCVA typically tracked improvements in reduction of macular edema by OCT. One study subject demonstrated progression from their baseline diabetic macular edema, initially improving during their treatment course but later progressing past their baseline OCT macular thickness at study day 150, 3 months off of intravitreal therapy. This study subject's BCVA initially improved 5 lines but later regressed to baseline by study day 150.

In this study, as shown graphically in FIGS. 10A through 10J, there was consistency in the lack of toxicity demonstrated by BCVA, OCT central macular thickness, lack of inflammatory response, or retinal pathology on clinical exam, FA, B-scan, or ERG. Overall, COMPOUND 1 was very well tolerated.

Interestingly, despite the end stage nature of the study subjects and the small study size, there appears to be a clear clinical indicator of efficacy with improvements in BCVA tracking anatomic improvements in OCT central macular thickness. Furthermore, the clinical improvements appear to endure at least 90 days past the last intravitreal treatment with COMPOUND 1 in nearly all study subjects that demonstrate improvements. The authors feel that a larger study is required to further evaluate and confirm the safety and efficacy of this new class of anti-angiogenic drugs and better understand the characteristics of its novel mechanism of action.

Effects of Ranibizumab and Compound 1 Alone and in Combination in Transgenic Mice Expressing Human VEGF Transgenic mice in which the rhodopsin promoter drives expression of human VEGF in photoreceptors (rho/VEGF mice) were randomized into separate treatment groups and studies were performed to provide the following comparisons:

| | |
|---|---|
| A | 25 µg Compound 1 (5 Animals) vs. Combination of 10µ ranibizumab + 25 µg Compound 1 (5 Animals) |
| B | 10 µg ranibizumab (5 Animals) vs. Combination of 10µ ranibizumab + 25 µg Compound 1 (5 Animals) |
| C | 25 µg Compound 1 (3 Amimals) vs. Phosphate Buffered Saline (vehicle/control) (3 Animals) |
| D | 10 µg ranibizumab (3 Animals) vs. Phosphate Buffered Saline (vehicle/control) (3 Animals) |

Pretreatment measurements of the area of subretinal neovascularization were made on each animal using image analysis by a masked observer. Each animal received its designated treatment in a single intraocular injection. Seven days post-dose, measurements of the area of subretinal neovascularization were again made and compared to the pre-dose measurements to determine the change in subretinal neovascularization area. Also, the animals were sacrificed and the retinas were dissected, immunostained with GSA lectin and examined by fluorescence microscopy.

Figure 11E:
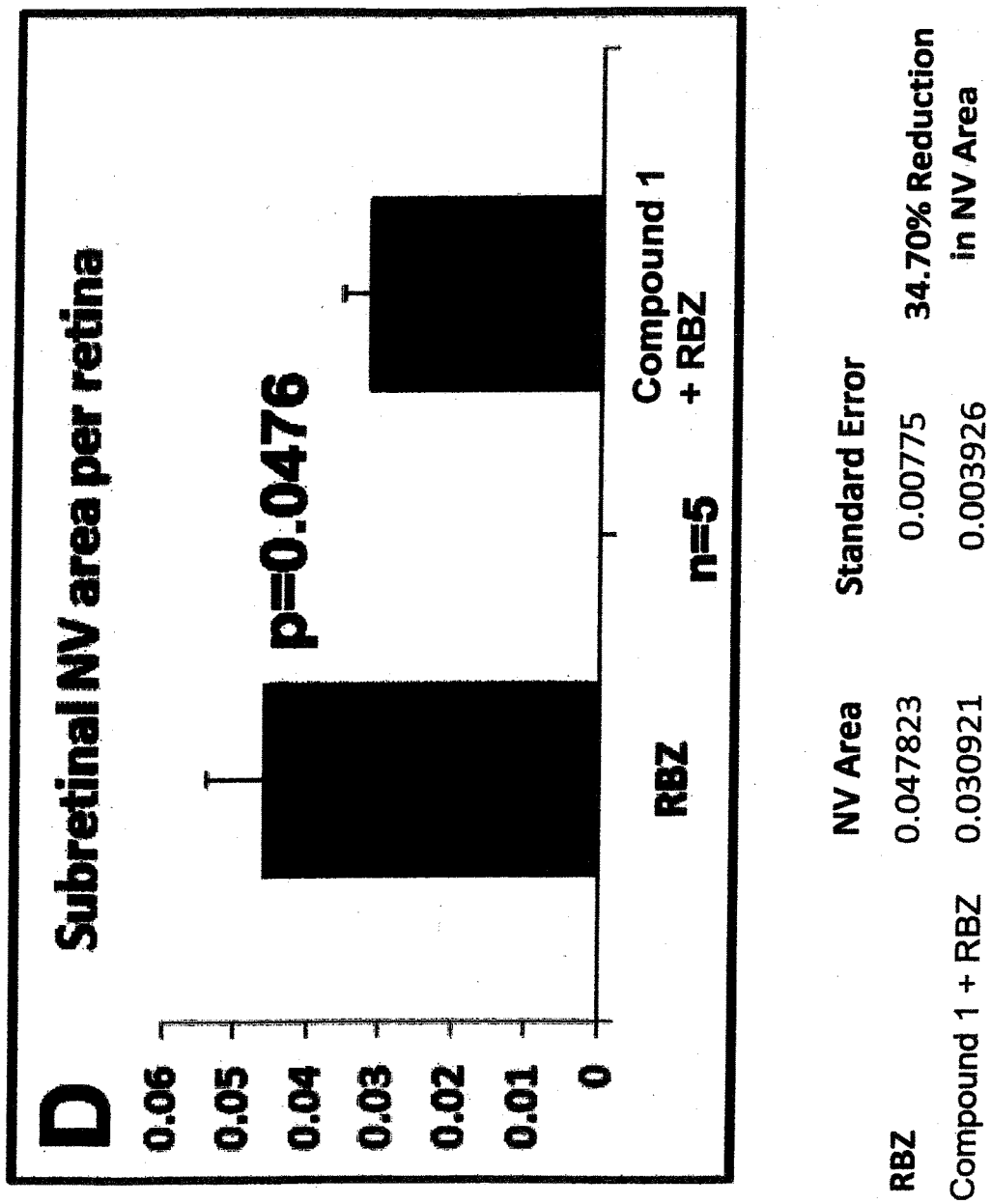
FIGS. 11A through 11D are bar graphs comparing the effects of ranibizumab and Compound 1 alone and in combination on retinal neovascularization in transgenic VEGF-producing mice.

FIG. 11A is a bar graph comparing the mean change in subretinal neovascularization area of animals receiving 25 µg Compound 1 (5 Animals) vs. animals receiving the combination of 10µ ranibizumab+25 µg Compound 1 (5 Animals). The animals receiving the combination of 10µ ranibizumab+25 µg Compound 1 exhibited a 35.34% greater reduction in subretinal neovascularization area than the animals receiving 25 µg Compound 1 alone. These data indicate that, at the doses tested, the combination of ranibizumab and Compound 1 was more effective in reducing subretinal neovascularization than Compound 1 alone.

FIG. 11B is a bar graph comparing the mean change in subretinal neovascularization area of animals receiving 10 µg ranibizumab (5 Animals) vs. animals receiving the combination of 10µ ranibizumab+25 µg Compound 1 (5 Animals). The animals receiving the combination of 10µ ranibizumab+25 µg Compound 1 exhibited a 34.70% greater reduction in subretinal neovascularization area than the animals receiving 10 µg ranibizumab alone. These data indicate that, at the doses tested, the combination of ranibizumab and Compound 1 was more effective in reducing subretinal neovascularization than Compound 1 alone.

Figure 11C:
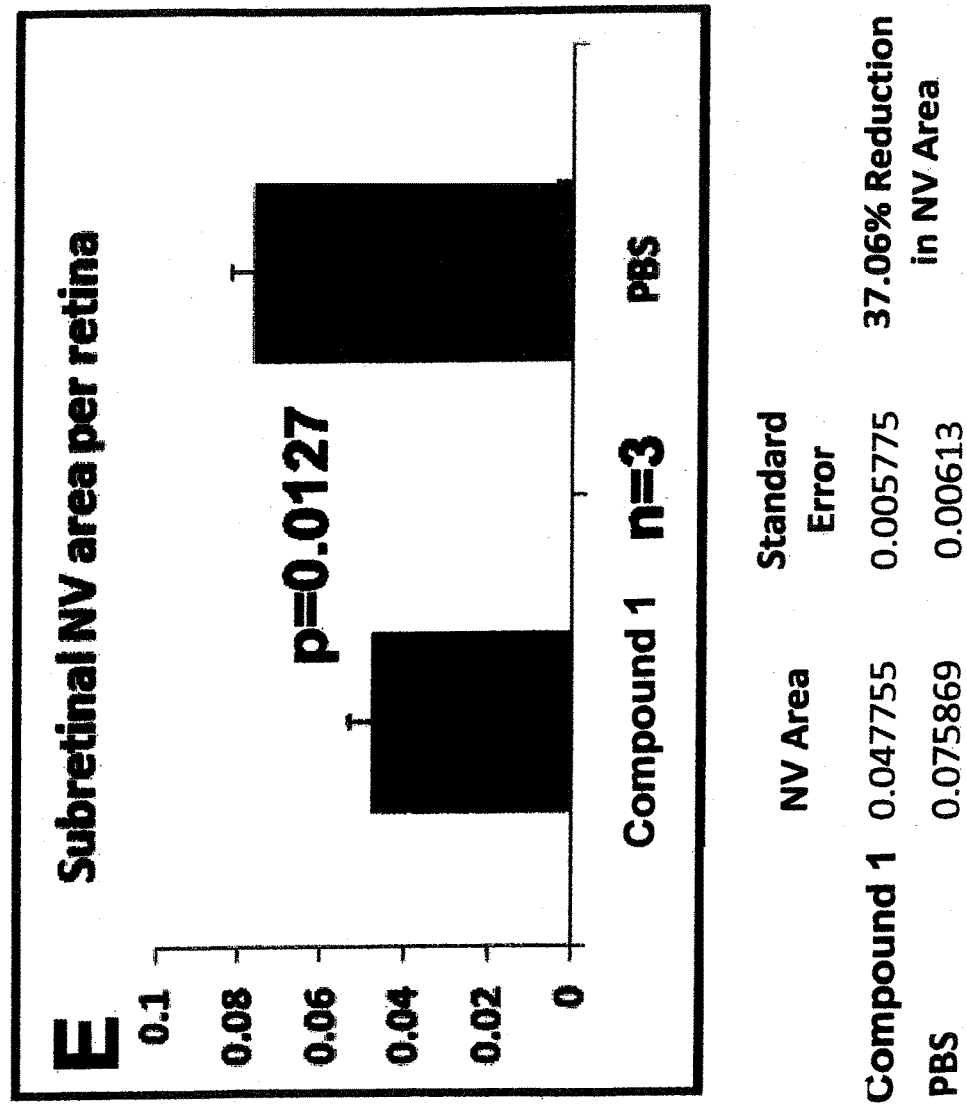

FIG. 11C is a bar graph comparing the mean change in subretinal neovascularization area of animals receiving 25 µg Compound 1 (3 Animals) vs. animals receiving Phosphate Buffered Saline (vehicle/control) (3 Animals). The animals receiving 25 µg Compound 1 exhibited a 37.06% greater reduction in subretinal neovascularization area than the control animals. These data indicate that, at the dose tested, Compound 1 was more effective than control in reducing subretinal neovascularization.

Figure 11D:
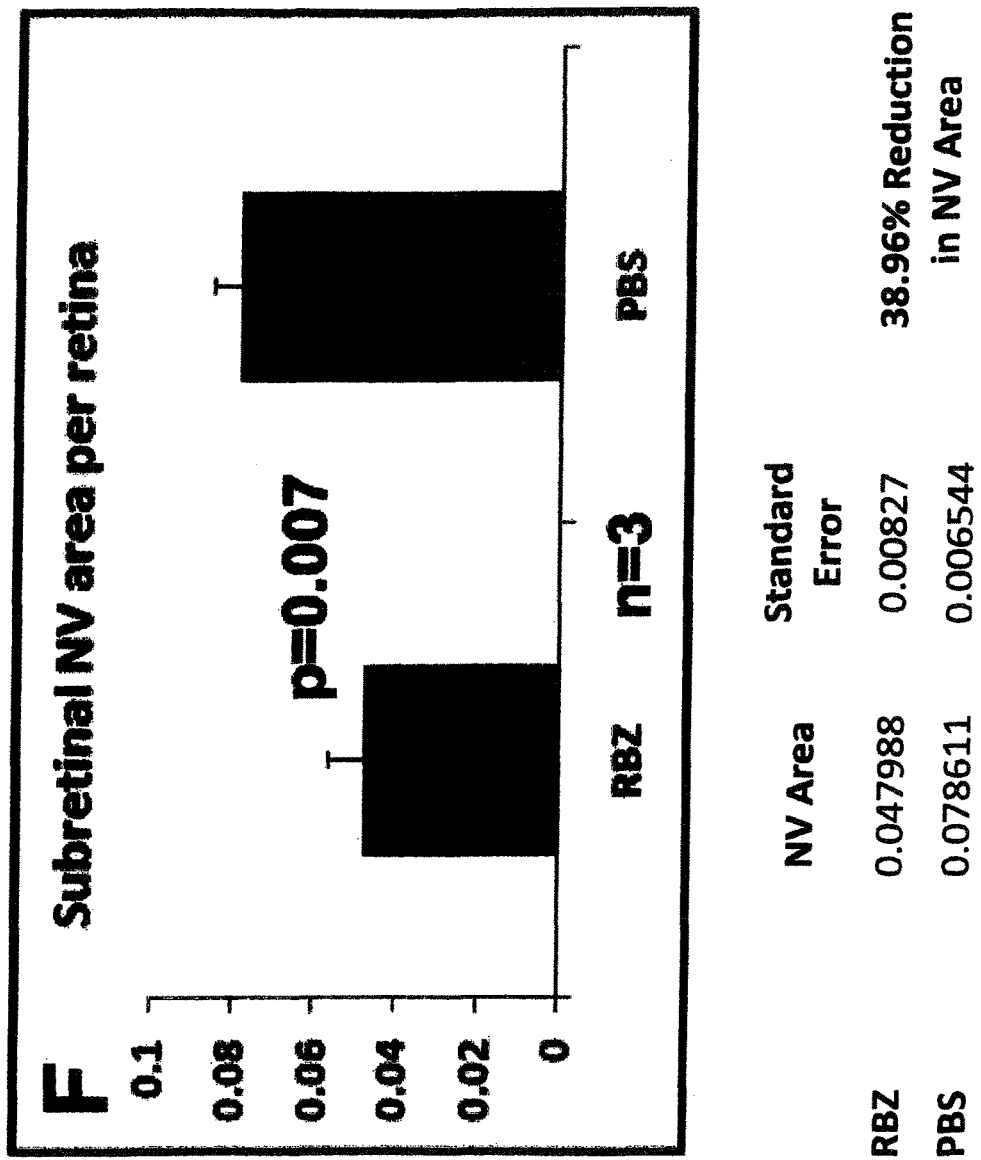

FIG. 11D is a bar graph comparing the mean change in subretinal neovascularization area of animals receiving 10 µg ranibizumab (3 Animals) vs. animals receiving Phosphate Buffered Saline (vehicle/control) (3 Animals). The animals receiving 10 µg ranibizumab exhibited a 38.96% greater reduction in subretinal neovascularization area than the control animals. These data indicate that, at the dose tested, ranibizumab was more effective than control in reducing subretinal neovascularization.

In summary, at the doses tested in these comparison studies, ranibizumab and Compound 1 each caused a statistically significant reduction in subretinal neovascularization area when administered alone. However, the combination of ranibizumab and Compound 1 caused significantly greater reduction in subretinal neovascularization area than either ranibizumab alone or Compound 1 alone. Based on these data, combination therapy using Compound 1 (or another integrin inhibiting compound of the present invention) in combination with a VEGF Trap (such as ranibizumab) has potential clinical benefit in patients suffering from neovascular eye diseases, As used herein, any reference to treating or treatment of a disease or disorder shall, unless otherwise noted, be construed to include preventing or prevention of the disease or disorder before it has occurred or been detected as well as treating the disease or disorder after it has occurred or has been detected.

It is to be appreciated that the invention has been described here above with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims. All publications and patent documents cited herein are hereby incorporated by reference in their entirety for all purposes to the same extent as if each were so individually denoted.

What is claimed is:

1. A method for inhibiting $\alpha_3\beta_1$-Integrin, $\alpha_5\beta_1$-Integrin, $\alpha_v\beta_3$-Integrin and $\alpha_v\beta_5$-Integrin, and/or other integrins and/or for inhibiting bFGF production in a human or animal subject in need thereof, said method comprising the step of:
    administering to the subject an effective amount of either:
    i) a peptide which comprises Glycinyl-Arginyl-Glycinyl-Cysteic-Threonyl-Proline-COOH or
    ii) a peptide which has the formula:

where X and $X_1$ are selected from: Phe-Val-Ala, -Phe-Leu-Ala, -Phe-Val-Gly, -Phe-Leu-Gly, -Phe-Pro-Gly, -Phe-Pro- Ala, -Phe-Val; or from Arg, Gly, Cysteic, Phe, Val, Ala, Leu, Pro, Thr and salts thereof and any combinations of D-isomers and L-isomers thereof.

2. A method according to claim 1 wherein the method is carried out to bring about at least one treatment, therapeutic effect or diagnostic effect selected from the group consisting of:

treating a microbial infection; deterring entry of microbes into cells; inhibiting angiogenesis; inhibiting vascularization of tumors or neoplasms; inhibiting the production or availability of VEGF; inhibiting the adhesion, migration and/or proliferation of cells; treating inflammation; treating cancer, treating metastasis; directing or delivering a therapeutic or diagnostic agent to a tumor, treating thrombosis; causing vitreolysis; causing vitreoretinal detachment; facilitating performance of a vitrectomy; and facilitating wound healing.

3. A method according to claim 1 wherein the method is carried out to treat a disorder of the eye which causes abnormal angiogenesis to occur within the eye.

4. A method for inhibiting $\alpha_3\beta_1$-Integrin, $\alpha_5\beta_1$-Integrin, $\alpha_v\beta_3$-Integrin and $\alpha_v\beta_5$-Integrin, and/or other integrins and/or for inhibiting bFGF production in a human or animal subject in need thereof, said method comprising the step of administering to the subject an effective amount of a compound having the following general formula:

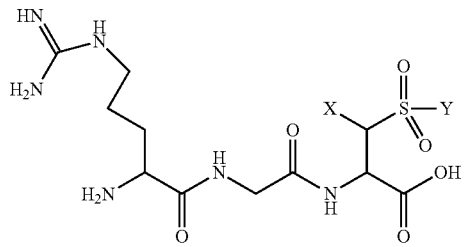

where X is selected from H, $C_1$-$C_6$ alkyl, Ph and $SO_3H$ and Y is independently selected from OH and $NH_2$.

5. A method for inhibiting $\alpha_3\beta_1$-Integrin, $\alpha_5\beta_1$-Integrin, $\alpha_v\beta_3$-Integrin and $\alpha_v\beta_5$-Integrin, and/or other integrins and/or for inhibiting bFGF production in a human or animal subject in need thereof, said method comprising the step of administering to the subject an effective amount of a compound having the following general formula:

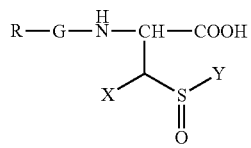

where X is selected from: H, $C_1$-$C_6$ alkyl, Ph or $SO_3H$; Y is selected from OH or $NH_2$.

6. A method for inhibiting $\alpha_3\beta_1$-Integrin, $\alpha_5\beta_1$-Integrin, $\alpha_v\beta_3$-Integrin, and $\alpha_v\beta_5$-Integrin, and/or other integrins and/or for inhibiting bFGF production in a human or animal subject in need thereof, said method comprising the step of administering to the subject an effective amount of a compound having the following general formula:

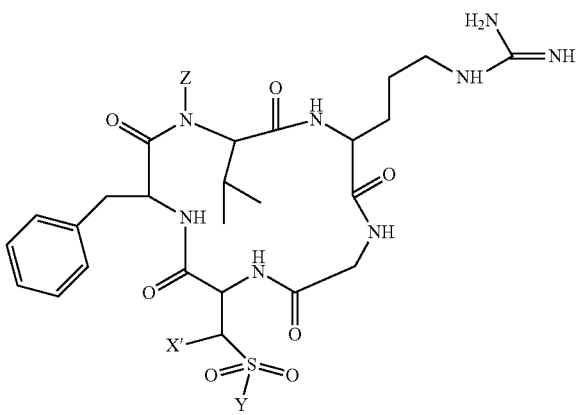

wherein X' is selected from H, $C_1$-$C_6$ alkyl, phenyl and —$SO_3H$;
Y is selected from OH and $NH_2$; and
Z is selected from H and methyl.

7. A method according to claim 1 wherein the method is carried out to treat a viral or other microbial infection.

8. A method according to claim 7 wherein the method is carried out to treat ebolavirus infection.

9. A method according to claim 1 further comprising administering to the subject an agent which inhibits, binds, traps or scavenges VEGF.

10. A method according to claim 9 wherein the agent which inhibits, binds, blocks or scavenges VEGF is selected from; bevacizumab (Avastin), ranibizumab (Lucentis) and aflibercept (Eylea).

11. A method according to claim 9 wherein the peptide is administered in an amount that is further effective to inhibit tyrosine kinase.

12. A method according to claim 9 wherein the peptide is administered in an amount that is further effective to cause posterior vitreoretinal detachment.

13. A method according to claim 9 wherein the method is carried out to treat a disorder which causes excessive vascularization of the retina of the subject's eye.

14. A method according to claim 13 wherein the disorder is selected from Wet Age-related Macular Degeneration, Diabetic Macular Edema, proliferative or non-proliferative diabetic retinopathy, idiopathic macular hole, vitreomacular traction, age related macular degeneration, choroidal neovascularization, vein occlusion, corneal neovascularization, ischemic optic nerve and rubiosis iridis.

15. A method according to claim 13 wherein the peptide is administered by intravireal injection.

16. A method according to claim 9 wherein the peptide and the agent which inhibits, binds, blocks or scavenges VEGF are combined and administered in a single intravitreal injection.

17. A method according to claim 9 wherein the peptide and the agent which inhibits, binds, blocks or scavenges VEGF are administered in separate intravitreal injections.

18. A method according to claim 1 wherein the peptide comprises Glycine-Arginine-Glycine-Cysteic(Acid)-Threonine-Proline.

19. A method according to claim 9 wherein the peptide comprises Glycine-Arginine-Glycine-Cysteic(Acid)-Threonine-Proline.

20. A method according to claim 19 wherein the agent which inhibits, binds, blocks or scavenges VEGF comprises bevacizumab (Avastin).

21. A method according to claim 19 wherein the agent which inhibits, binds, blocks or scavenges VEGF comprises ranibizumab (Lucentis).

22. A method according to claim 19 wherein the agent which inhibits, binds, blocks or scavenges VEGF comprises aflibercept (Eylea).

23. A method according to claim 1 wherein the method is carried out to inhibit angiogenesis in a vascularized tumor.

24. A method according to claim 23 wherein the tumor is cancerous.

25. A method according to claim 1 wherein the method is carried out to deter metastasis.

26. A method according to claim 1 wherein the peptide is administered in an amount that is effective to deter bFGF production.

27. A method according to claim 1 wherein the peptide is administered in an amount that is effective to cause liquefaction of vitreous humor.

28. A method according to claim 1 wherein the peptide is administered in an amount that is effective to cause posterior vitreo-retinal detachment.

\* \* \* \* \*